US007465469B2

(12) United States Patent
Ben-Yehoshua

(10) Patent No.: US 7,465,469 B2
(45) Date of Patent: Dec. 16, 2008

(54) MICROBIOCIDAL FORMULATION COMPRISING ESSENTIALS OILS OR THEIR DERIVATIVES

(75) Inventor: Shimshon Ben-Yehoshua, Kiryat-Ono (IL)

(73) Assignee: State of Israel, Ministry of Agriculture & Rural Development Agricultural Research Organization, The Volcani Center, Bet Dagan (IL)

( * ) Notice: Subject to any disclaimer, the term of this patent is extended or adjusted under 35 U.S.C. 154(b) by 235 days.

(21) Appl. No.: 10/491,491

(22) PCT Filed: Oct. 3, 2002

(86) PCT No.: PCT/IL02/00808

§ 371 (c)(1),
(2), (4) Date: Jun. 24, 2004

(87) PCT Pub. No.: WO03/028451

PCT Pub. Date: Apr. 10, 2003

(65) Prior Publication Data

US 2004/0234662 A1 Nov. 25, 2004

(30) Foreign Application Priority Data

Oct. 4, 2001 (IL) .................................... 145767

(51) Int. Cl.
*A23B 7/16* (2006.01)

(52) U.S. Cl. ....................... 426/331; 426/332; 426/333; 426/335; 426/615

(58) Field of Classification Search ................. 426/331, 426/332, 333, 335, 615
See application file for complete search history.

(56) References Cited

U.S. PATENT DOCUMENTS

| 4,230,687 A | 10/1980 | Sair et al. |
| 4,379,168 A | 4/1983 | Dotolo |
| 4,452,805 A | 6/1984 | Hayes |
| 5,296,245 A | 3/1994 | Clarke et al. |

(Continued)

FOREIGN PATENT DOCUMENTS

ES 2081262 A * 2/1996

(Continued)

OTHER PUBLICATIONS

Ben-Yehoshua, S. et al. "Preformed and Induced Antifungal Materials of Citrus Fruits in Relation to the Enhancement of Decay Resistance by Heat and Ultraviolet Treatments", *J. Agric. Food Chem.*, vol. 40 pp. 1217-1221, 1992.

(Continued)

*Primary Examiner*—Helen F Pratt
(74) *Attorney, Agent, or Firm*—Nath Law Group; Susanne M. Hopkins; Ari G. Zytcer

(57) ABSTRACT

The present invention deals with a microbiocidal aqueous formulation comprising: (i) an effective amount of at least one essential oil component, or derivatives thereof, said derivatives thereof obtained by exposure to light or by oxidation, or mixtures thereof; and (ii) at least one additional stabilizer selected from the group consisting of ethanol in an amount of from 10% to about 50%, an emulsifier, an antioxidant, or an encapsulating agent. The invention is further directed to a method for inhibiting microbial development using said microbiocidal aqueous formulation.

13 Claims, 15 Drawing Sheets

EFFECT OF SEVERAL TREATMENTS ON THE PHYTOALEXIN CONTENT OF LEMON FRUIT FLAVEDO

*Five μl of this chemical was injected into the albedo just below the flavedo tissue.

U.S. PATENT DOCUMENTS

| | | | |
|---|---|---|---|
| 5,334,619 A | | 8/1994 | Vaughn et al. |
| 5,342,420 A | * | 8/1994 | Bosses ..................... 96/222 |
| 5,456,985 A | | 10/1995 | Zgoulli et al. |
| 5,466,471 A | | 11/1995 | Yatka |
| 5,597,595 A | * | 1/1997 | DeWille et al. ............. 426/74 |
| 5,753,593 A | | 5/1998 | Pullen et al. |
| 5,935,826 A | | 8/1999 | Blue et al. |
| 5,951,992 A | | 9/1999 | Wilkins, Jr. |
| 5,958,490 A | | 9/1999 | Solar et al. |
| 6,086,917 A | | 7/2000 | Trubiano et al. |
| 6,451,861 B1 | * | 9/2002 | Pimentel et al. ............ 514/703 |
| RE38,813 E | * | 10/2005 | Clum et al. ................ 514/529 |
| 2006/0030511 A1 | * | 2/2006 | Holland et al. ............. 510/441 |

FOREIGN PATENT DOCUMENTS

| | | |
|---|---|---|
| HU | P960234 A | 2/1998 |
| HU | P0000339 A | 11/2001 |
| JP | 59132876 | 7/1984 |
| JP | 62111675 | 5/1987 |
| JP | 10117680 | 5/1998 |
| RU | 1777889 A1 | 11/1992 |
| SU | 1762934 A1 | 9/1992 |
| WO | 00/21364 A3 | 4/2000 |
| WO | 00/49865 A2 | 8/2000 |
| WO | 00/49880 A1 | 8/2000 |

OTHER PUBLICATIONS

Rodov, V. et al. "Ultraviolet Illumination Induces Scoparone Production in Kumquat and Orange Fruit and Improves Decay Resistance", *J. Amer. Soc. Hort. Sci*, vol. 117(5) pp. 788-792, 1992.

Wilson, C. et al. "Postharvest Biological Control of *Penicillium* Rots of Citrus with Antagonistic Yeasts and Bacteria", *Scientia Horticulturae*, vol. 40 pp. 105-112, 1989.

Ben-Yehoshua, S. et al. "Preformed Antifungal Compounds of Citrus Fruit: Effect of Postharvest Treatments with Heat and Growth Regulators", J. Agric. Food Chem., vol. 43 pp. 1062-1066, 1995.

Rodov, V. et al. "Preformed Antifungal Compounds of Lemon Fruit: Citral and Its Relation to Disease Resistance", *J. Agric. Food* Chem., vol. 43 pp. 1057-1061, 1995.

Chalchat, J.C. et al. "Photochemical Hydroperoxidation of Terpenes. Antimicrobial Activity of $\alpha$-Pinene, $\beta$-Pinene and Limonene Hydroperoxides", J. Essent. Oil. Res., vol. 12 pp. 125-134, 2000.

Aureli, P. et al. "Antimicrobial Activity of Some Plant Essential Oils Against *Listeria monocytogenes*", *Journal of Food Protection*, vol. 55(5) pp. 344-348, 1992.

Nandi, B. et al. "Preservation of High Moisture Barley Grains With Citral and Allyl Caproate and Preliminary Acceptability Tests with Piglets", *Acta Agriculturae Scandinavica*, vol. 27 pp. 105-109, 1977.

Mallick, A.K. et al. "Deterioration of Stored Rough Rice-Preservation and Palatability of Citral and Propionic Acid Treated Grains", *Acta Agriculturae Scandinavica*, vol. 32 pp. 177-187, 1982.

Ghosh, J. et al. "Preservation of High-Moisture Wheat by Some Antifungal Volatile Compounds and Palatability Tests with Rats", *Acta Agric Scand*, vol. 35 pp. 245-254, 1985.

Arora, R. et al. "The Application of Essential Oils and their Isolates for Blue Mould Decay Control in *Citrus reticulata* Blanco", Journal of Food Science and Technology, vol. 14 pp. 14-16, 1977.

Papadopoulou, M.E. "Postharvest-applied Agrochemicals and Their Residues in Fresh Fruits and Vegtables", *Journal of the Association of Official Analytical Chemists*, vol. 74(5) pp. 745-765, 1991. Abstract.

Kurita, N. et al. "Synergistic Antimicrobial Effect of Ethanol, Sodium Chloride, Acetic Acid and Essential Oil Components", *Agric. Biol. Chem.*, vol. 47(1) pp. 67-75, 1983.

Kim, J., et al., "Antibacterial Activity of Some Essential Oil Components against Five Foodborne Pathogens", *J. Agric. Food Chem.*, vol. 43, pp. 2839-2845, (1995).

Ritenour, M.A., et al., "Postharvest Decay Control Recommendations for Florids Citrus Fruit", *University of Florida IFAS Extension*, pp. 1-5, May 1993.

Aharoni, Y., et al., "Hinokitiol ($\beta$-thujaplicin), for postharvest decay control on 'Galia' melons", *New Zealand Journal of Crop and Horticultural Science*, vol. 21, pp. 165-169, (1997).

* cited by examiner

FIG. 12 THE EFFECT OF LIMONENE HYDROXYPEROXIDE (LHPO) PREPARED WITH A MOLYBDATE CATALYST ON DECAY OF LEMON FRUIT INOCULATED WITH *Penicillium digitatum*.

Candida were grown for 48 hrs at 37°C. Their density was then determined at OD 650 nm Series 1 (x diluted 1:5). Series 2 x diluted 1:10.

MICROBIOCIDAL FORMULATION COMPRISING ESSENTIALS OILS OR THEIR DERIVATIVES

FIELD OF THE INVENTION

The present invention concerns means to inhibit microbial development. More specifically, the present invention concerns formulations and methods for inhibiting microbial development in perishable agricultural produce, household and human hygiene comprising of essential oil components or their derivatives obtained by exposure to irradiation of light or by oxidation, together with stabilizers.

BACKGROUND OF THE INVENTION

The decay of perishable agricultural produce is caused by microbial infection. Such produce is typically kept for long enough periods of time during which conditions allowing for the propagation of various microorganisms exist and accordingly, very often, a high percent of the produce becomes infected. In addition to the obvious substantial financial loss due to such decay, some of these microorganisms produce toxic and carcinogenic metabolites, which are harmful to humans.

Control of pathogen infection of perishable agricultural produce is achieved today mainly by exogenous application of synthetic fungicides and/or bactericides. However, these synthetic chemicals have toxic residues in the produce. Furthermore, development of resistant strains of microorganisms has also been observed. As a result, several such fungicides and bactericides are being phased out by regulating agencies. The residual toxicity and the potential phasing out gave rise to the development of alternatives to the synthetic chemicals presently used for prevention of decay.

Several of the alternatives are described below. For example, irradiating the agricultural produce by ultraviolet light (Ben-Yehoshua, S., Rodov, V, Kim, J. J. and Carmeli, S., 1992. Preformed and induced antifungal materials of citrus fruits in relation to the enhancement of decay resistance by heat and ultraviolet treatments. *J. Agric. Food Chem.*, 40:1217-1221; Rodov, V., Ben-Yehoshua, S., Kim, J. J., Shapiro, B. and Ittah, Y, 1992. Ultraviolet illumination induces scoparone production in kumquat and orange fruit and improves decay resistance. *J. Amer. Soc. Hortic. Sci*, 117: 188-192), or exposing the produce to antagonistic yeasts (Wilson, C. L. and Chalutz, E., 1989. Postharvest biocontrol of *Penicillium* rots of citrus with antagonistic yeasts and bacteria. *Scientia Horticulturae*, 40: 105-112). However U.V. irradiation may be phytotoxic and the biocontrol with the antagonistic yeast is not yet well accepted commercially, possibly because of inadequate control of the pathogens. Furthermore, these methods have various drawbacks and some of the relevant health authorities have not yet approved some of them.

Citrus fruit, as well as various other plants, possess some endogenous resistance against pathogens owing to the production of anti-microbial substances in the plant tissues {Ben-Yehoshua, S., Rodov, V, Kim, J. J. and Carmeli, S., (1992) Preformed and induced antifungal materials of citrus fruits in relation to the enhancement of decay resistance by heat and ultraviolet treatments. *J. Agric. Food Chem.*, 40:1217-1221; Ben-Yehoshua, S., Rodov, V, Fang, D. Q., and Kim, J. J., (1995) Preformed antifungal compounds of citrus fruit: effect of postharvest treatments with heat and growth regulators. *J. Agric. Food Chem.* 43: 1062-1066; Rodov, V., Ben-Yehoshua, S., Fang, D. Q., and Kim, J. J., (1995) Preformed antifungal compounds of lemon fruit: citral and its relation to disease resistance. *J. Agric. Food Chem.* 43: 1062-1066). It has been previously shown that these substances include essential oil components, which exhibit a broad range of anti-microbial activity. U.S. Pat. Nos. 5,334,619 and 5,958,490 describe the use of several natural occurring oils as active agents for preventing decay in post-harvest agricultural products. However only few of the essential oil components have microbiocidal activity.

Citral [3,7-dimethyl-2,6-octadienal] is an essential oil component which is naturally produced in several kinds of citrus fruits as well as in some other plants such as lemon grass and eucalyptus. Citral is an unsaturated aldehyde from the terpene series and is composed of an isomeric mixture of geranial and neral. Because of its intense lemon aroma and flavor, citral has been extensively used in food and cosmetic industries. Citral is recognized as a safe food additive and is approved for use in food by the U.S. Food and Drug Administration. Citral has also been shown to exhibit a very effective and broad range of antimicrobial and antifungal activity. In fact, Ben Yehoshua et al (1992) and Rodov et al (1995) have shown that citral is the most active constitutive antifungal compound in lemon fruit.

Limonene, 1-methyl-4-(1-methylethenyl)cyclohexene (known also as p-mentha-1,8-diene) is another example of an abundant essential oil component, is which may be extracted from glands of flavedo of citrus fruit. U.S. Pat. No. 4,379,168 and U.S. Pat. No. 5,951,992 describe the use of limonene as an insecticide and pesticide, respectively. However in its pure form it has very low antifungal activity. Chalchat et al. (Chalchat, J. C., Chiron, F., Garry, R. Ph. and Lacoste (2000, J. Essent. Oil Res. 12, 125-134) disclose antimicrobial activity of limonene hydropeoxide against Human pathogens.

Aureli et al. (Aureli, P., Costantini, A. and Zolea, S., 1992. Antimicrobial activity of some plant essential oil against *Listeria monocytogenes*. *J Food Protection*, 55:344-348) showed that some essential oil components have strong activity against pathogenic bacteria such as *Listeria* and suggested their use in preventing the infection of food by *Listeria*.

Several attempts have been made to use citral to control decay of various agricultural produce. It was shown that Citral could reduce grain deterioration of *Aspergillus* inoculated high moisture barley (Nandi, B., Thomke S. and Fries, N., 1977. Preservation of high moisture barley grains with citral and allyl caproate and preliminary acceptability tests with piglets. *Acta Agric. Scand*, 27:105-109), rough rice (Mallick, A. K. and Nandi, B., 1982. Deterioration of stored rough rice. IV. Preservation and palatability of citral and propionic acid treated grains. *Acta Agric. Scand.*, 32:177-187) and wheat (Ghosh, J. and Nandi, B., 1985. Preservation of high moisture wheat by some antifungal volatile compounds and palatability tests with rats. *Acta Agric. Scand.*, 35:245-254). Arora and Pandey (Arora, R. and Pandey, G. N., 1977. The application of essential oils and their isolates for blue mold decay control in *Citrus reticulata* Blanco. *J. Food Sci. and Tech* 14:14-16) reported that citral, geraniol and other essential oil compounds reduce the blue-mold decay of *Citrus reticulata* fruit. The inventor of the present invention (Ben-Yehoshua, S., Rodov, V., Kim, J. J. and Carmeli, S., 1992. Preformed and induced antifungal materials of citrus fruits in relation to the enhancement of decay resistance by heat and ultraviolet treatments. *J. Agric. Food Chem.*, 40:1217-1221) showed that application of exogenous Citral to *Penicillium*-inoculated lemons significantly inhibited their decay.

In most cases of the prior use of essential oil components to prevent decay of agricultural produce, the essential oil component was applied to the produce in an aqueous emulsion.

Although partial prevention of the produce's decay was achieved by the use of such substances, essential oil components, including citral and geraniol, are still not used commercially for decay control of perishable agricultural produce. One main reason for not using those substances is that their application to perishable produce, in a concentration effective against the microorganisms, inflicts damage to the produce, which may cause decay later on. For example, essential oils inflict peel damage in fruit and color changes in meat. This damage may be severe and results in a significant decay of the treated produce after a relatively short period of time. Another reason for the lack of their commercial use is their instability as many of these essential oils are unstable and tend to decompose prior to carrying out their bactericidal activity.

SUMMARY OF THE INVENTION

The present invention is based on the fact that food-grade essential oil components or their derivatives obtained by exposure to irradiation of light or by oxidation, may be used as the active ingredient in a stable effective microbiocidal formulation for the inhibition of microbial development. In such a formulation the known phytotoxic damage of the essential oil components is prevented and the stability of the essential oil component or its derivatives is prolonged, resulting in an environmentally friendly microbiocidal composition.

Thus one object of the present invention is to provide a novel microbiocidal aqueous formulation comprising:
  (i) an effective amount of at least one essential oil component, or derivatives thereof, said derivatives thereof obtained by exposure to light or by oxidation, or mixtures thereof; and
  (ii) at least one additional stabilizer selected from the group consisting of ethanol in an amount of from 10% to about 50%, an emulsifier, an antioxidant, or an encapsulating agent.

The amount of added ethanol is from about 10 to about 50%. The essential oil component is selected from the group of monoterpene hydrocarbons, sesquiterpenes, oxygenated terpene derivatives, non-terpene derivatives such as aldehydes, alcohols, acids and phenolics. The concentration of the essential oils in the aqueous microbiocidal composition is from about 0.1% to about 1% (v/v). The concentration of the derivative of the essential oil obtained by exposure to light is from about 1000 μL L$^{-1}$ to about 12,000 μL L$^{-1}$. The microbiocidal composition may further comprise an additional amount of another biocide in a small amount which by itself is not sufficient for inhibiting microbial development.

It is a further object of the present invention to provide a method for inhibiting microbial development in perishable agricultural produce by applying a microbiocidal aqueous formulation comprising:
  (i) an effective amount of at least one essential oil component, or derivatives thereof, said derivatives thereof obtained by exposure to light or by oxidation, or mixtures thereof; and
  (ii) at least one additional stabilizer selected from the group consisting of ethanol in an amount of from 10% to about 50%, an emulsifier, an antioxidant, or an encapsulating agent.

The amount of added ethanol is from about 10 to about 50%. The essential oil component is selected from the group of monoterpene and sesquiterpene hydrocarbons, oxygenated terpene derivatives, non-terpene derivatives such as aldehydes, alcohols, acids and phenolics. The formulation may further comprise another pesticide in a small amount which on itself is not sufficient for inhibiting microbial development.

A further object of the present invention is to provide methods for inhibiting microbial development in household by applying the microbiocidal aqueous formulation of the present invention either alone or together with commonly used detergents.

Still yet a further object of the present invention is to provide use of the microbiocidal formulation for human hygiene where the essential oils or derivatives thereof together with suitable additives is added to soap bars, hygiene, dish washing detergents, mouth washes disinfecting or cosmetic applications.

It is still a further object of the present invention to provide use of the microbiocidal formulation as a nutraceutical for relieving or treating minor infections caused by microbials, as well as providing benefits to human health.

BRIEF DESCRIPTION OF THE DRAWINGS

In order to understand the invention and to see how it may be carried out in practice, a preferred embodiment will now be described, by way of non-limiting example only, with reference to the accompanying drawings, in which.

DETAILED DESCRIPTION OF THE INVENTION

Figure 1:
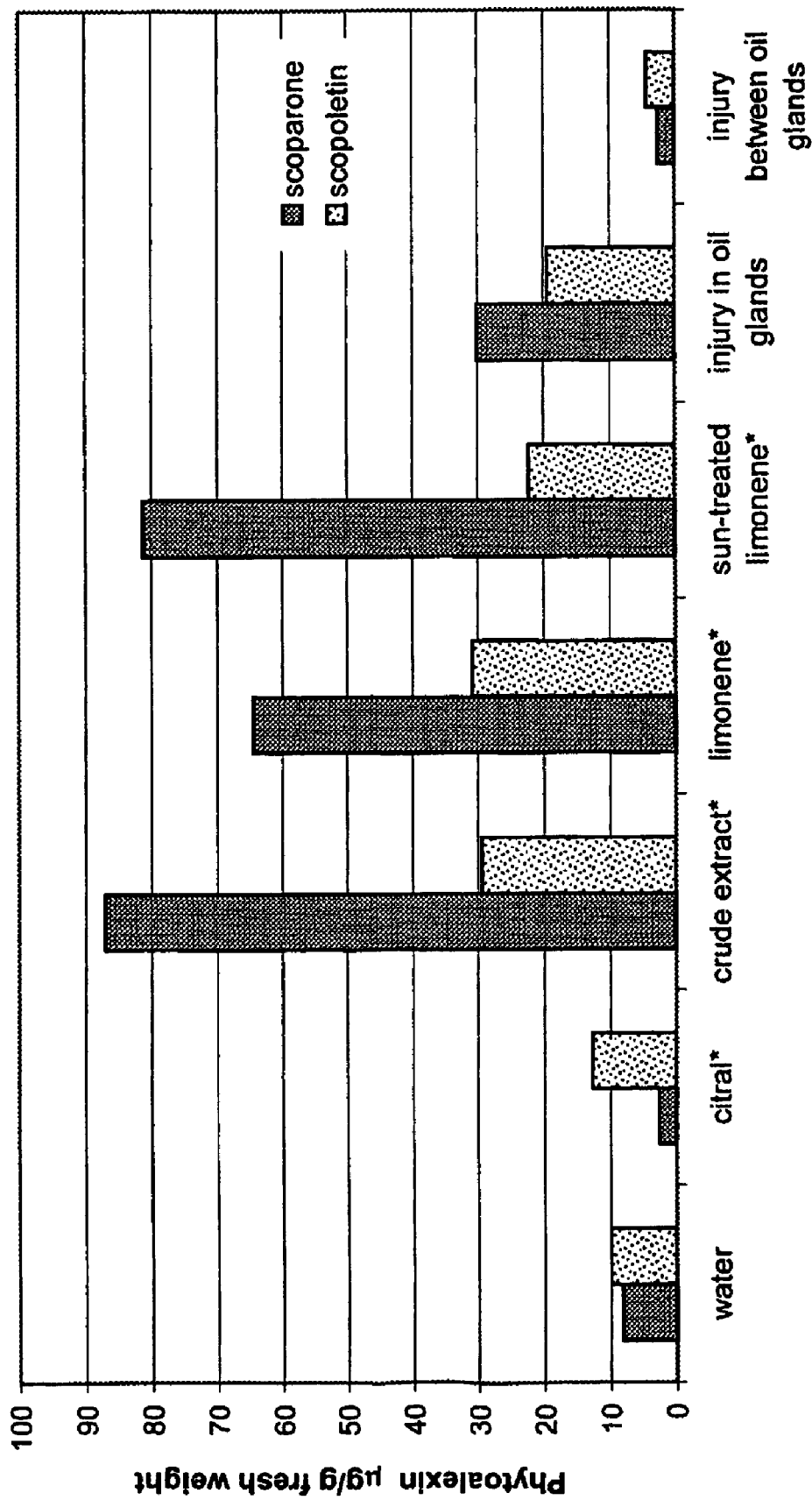
FIG. 1 shows the induction of scoparone production in mature green lemon by injecting sun treated limonene, limonene or citral to albedo or by releasing the contents of the oil glands in mature-green lemons.

As stated above the present invention provides an environmentally friendly microbiocidal formulation effective in preventing decay in agricultural produce, in household, for human hygiene and as a nutraceutical composition. The aqueous microbiocidal formulation comprises of as the active ingredient, at least one essential oil component or derivatives thereof obtained by exposure to light or by oxidation, or mixtures of such essential oils and/or their derivatives, and at least one additional stabilizer selected from the group consisting of ethanol in an amount of from about 10% to about 50%, an emulsifier an antioxidant or an encapsulating agent. The role of the stabilizer is to stabilize the essential oil components from decomposing prior to performing their microbiocidal action and/or prevent and/or reduce the phytotoxicity of these compounds. The microbiocidal essential oil component is selected from the group of monoterpene hydrocarbons and sesquiterpenes, oxygenated terpene derivatives and nonterpene derivatives, such as aldehydes (citral or nonanal), alcohols (octanol, nonanol), and phenolics (cravacrol). The aqueous microbiocidal formulation may be used for an effective control and inhibition of microbial development. All essential oil components are well known to be food-grade components. It should further be stressed that all components of the aqueous microbiocidal formulation are food-grade, and do not pose any harm to the human body. One particular wide potential use is for protecting perishable agricultural produce from decay caused by microbials. Agricultural produce may include for example any fresh food produce, which may be spoiled as a result of microbial infection, such as fruits, vegetables, meat or fish. Other potential uses for appropriate formulation may be in any case that an effective protection from microbials is needed such as in household use, body hygiene or nutraceuticals. For household use the aqueous microbiocidal formulation may be used alone or together with commercial detergents. For use of the components of the essential oils or their derivatives for body hygiene, an effective amount of this essential oil components or its derivative may be incorporated into soap bars, a cleansing formulation, detergents for washing dishes, mouth wash or composition or a deodorizing solution or composition. An effective amount of an essential oil component of the present invention, particularly for the essential oils selected from citral, perillaldehyde or limonene, may also be part of a composition used as a nutraceutical. Such nutraceutical composition may achieve two effects, namely protect against biocidal infections as well as yield additional health benefit such as introduce anti-cancer activity. Several formulations of the present invention comprising essential oils such as citral, limonene, geraniol, menthol, carvone, perillaldehyde were found to act as anti-cancer agents and reduce the level of cholesterol and LDL. Citral and citronellal are known to calm and relax emotions and aid the body for proper digestive function. Such essential oil components are known as phytonutrients or functional foods.

Some of the essential oil components are known in the prior art as effective in combating microbials, especially in agricultural produce. However, essential oil components suffer from two inherent problems, which limited their practical use so far. One problem is associated with their limited stability, due to oxygenation process causing rapid disintegration of the essential oils upon exposure to oxygen. Thus, although their use as potent microbiocides was known, effectively such use was limited due to its short term. Use of rather large quantities of an essential oil in order to prolong its microbiocidal effect ultimately leads to the second drawback associated with their use: Exposure of fruits to high concentrations of essential oils, particularly if the mixture does not form a real solution, causes damage to the produce.

It has been found now that when the essential oil components are applied as the active component of a microbicidal composition together with at least one additive, which stabilizes or dissolves the essential oil components, a stable and effective microbiocidal composition is obtained which does not cause any damage to the produce. These additives are selected from ethanol, an antioxidant, an emulsifier or an encapsulating agent. Each of these additives protects the essential oils components in a different mechanism. The ethanol, which is biocidal by itself, is added in order to dissolve the essential oil component and prevent phytotoxicity and should be present in an amount of from about 10% to about 50%. The emulsifier keeps forming a microcollolidial solution that helps in the prevention of the phytotoxcity of the essential oil components. The emulsifiers may be chosen from the group comprising of alkylaryl polyether alcohol (DX), polyoxyethylene sorbitan monolaurate (Tween 20), polyoxyethylene sorbitan monooleate (Tween 80), octyl-phenyl polyether alcohol (Triton 100). Some of these emulsifiers are food-grade, e.g. Tween 20. The concentration of the emulsifiers should be above 0.1% (w/w).

The antioxidant reduces the oxidation rate of the essential oils leading to their decomposition. It further reduces the inherent phytotoxicity of the essential oil. The antioxidant may be chosen from the group comprising of compounds such as but not limited to: butylated hydroxyanisole (BHA), ascorbic acid, isoascorbic acid, α-tocopherol, butylated hydroxytoluene (BHT), β-carotene or their mixtures. Preferred concentrations of the antioxidant in the formulation of the invention are in the range of from about 0.05% to about 0.8% (w/v). The effect of the antioxidant in reducing the phytotoxicity of the essential oil for the case of the addition of BHA to citral is demonstrated in Table 1, showing the Peel Blemish Index, where it should be understood that BHA by itself did not cause any blemish.

The peel blemish index is determined by $$\text{Index} = \frac{\sum(\text{score } X \text{ number of fruit with given score})}{(\text{total number of fruit})}$$

The blemish score is 0 =no blemishes; 1=light blemishes; 2=moderate blemishes; and 3=severe blemishes.

TABLE 1

Effect of a 1-minute dip of the antioxidant BHA on peel blemishes in lemon fruit kept at 20° C. for 20 days.

| Citral (%) | BHA (%) | Peel Blemish Index |
|---|---|---|
| 0.0 | 0.0 | 0.10 |
| 0.5 | 0.0 | 0.48 |
| 0.5 | 0.05 | 0.14 |
| 0.5 | 0.1 | 0.05 |
| 0.5 | 0.3 | 0.00 |
| 0.5 | 0.6 | 0.00 |
| 1.0 | 0.0 | 0.90 |
| 1.0 | 0.3 | 0.52 |

The encapsulating agents added to the formulation, complex together with the essential oil components, thus preventing their degradation and prolonging their period of effective microbiocidal action. The encapsulating agent may be any kind of food grade matrix or polymer made of carbohydrate or protein or other matrix such as, but not limited to cornstarch, maltodextrin, β-cyclodextrin, silica gel, casein, chitosan and their mixtures. Low molecular weight polyethylene and various waxes may also act as encapsulation materials. In fact it was found that adding citral to various wax formulations that did not comprise any fungicides enhanced the effectiveness of citral in reducing both decay as well as phytotoxicity. The addition of cyclodextrin to citral resulted also in longer life of the citral on the surface of the treated orange fruit. Preferred concentrations of the encapsulating agent in the formulation of the invention are in the range of from about 0.1 to about 0.8% (w/v).

The addition of an emulsifier reduces the inherent phytotoxicity of the essential oil. This effect is shown by the blemish index of the essential oil citral by the addition of emulsifier as demonstrated in Table 2.

TABLE 2

Summary of trials evaluating phytotoxicity of citral solutions comprising emulsifiers (1:1 ratio with citral)[1].

|  | 0.5% Citral | 1.0% Citral |
|---|---|---|
| DX | 0 | 0 |
| Tween 80 | 0 | 0 |
| Tween 20 | 0 | 0 |
| Triton X 100 | 0 | 0 |
| Gelatin | 1.0 | 1.4 |
| Sodium lauryl sulfate (SLS) | 1.3 | 1.6 |
| Gum arabic | 1.2 | 1.9 |

[1] The fruit were dipped for 1 minute in the emulsion and then kept for one month at 20° C.
Phytotoxcity was measured as in Table 1.

It should be noted that in addition to the at least one essential oil component, its derivatives obtained by exposure to irradiation or mixtures thereof, the microbiocidal composition may comprise another biocide in a very low concentration. Such a low concentration of the biocide is not sufficient to prevent microbial damage on its own, however together with the essential oils of the present invention or their derivatives, the microbial decay may be prevented. Non limiting examples of such biocides may be imazalil, thiabendazole, panoctine, rovral, prochloraz, sodium orthophenylphenate, metalaxyl, phosetyl-Al, captan, oxyquinoline, dicloran benzalkonium chloride, canon, thiophanate-methyl, triforine, carbendazim, triademinol, vinclozolin, etaconazole, or mixture thereof. The concentration of such added pesticides may be from about 5 ppm to about 100 ppm. The use of such a composition comprising a combination of an essential oil component or its derivatives obtained by exposure to irradiation of light together with a small amount of fungicide will enable two important benefits:

1. Reducing the toxic residue of the biocide, which is an important demand of all health authorities for all toxic fungicides.

2. Controlling the development of resistance of the pathogen to the biocide. This specific point would be achieved by the use of the new formulation with or without the biocide component. In fact use of a different biocide, which may have a different mode of action, even for a relatively short time, is considered the recommended way of controlling the resistant population to biocides.

The essential oil components according to the present invention may be produced synthetically, or may be a plant-extract preparation comprising a plurality of components of essential oils, i.e. mixtures thereof. It may also be a purified natural essential oil preparation enriched with a single essential oil component or any combination thereof. Preparations containing natural essential oils may be produced from various plants such as citrus fruits, lemon grass and eucalyptus trees. Particular non-limiting examples of essential oil compounds are citral, 1-octanol, heptanol, nonanol, geraniol, octanal, nonanal, decanal, perillaldehyde, perillalcohol, citronellol, citronellal, carvone, carveol, linalool, vanillin, cinnamic aldehyde, cinnamic acid, eugenol, menthol, limonene, carvacrol, terpineol, thymol, vanillin and camphor. In cases according to the invention where the essential oil is derivatized by exposure to light, such derivatization may be done on synthetically produced essential oil, on naturally extracted essential oil or an a crude extract comprising a plurality of essential oil. In the latter case, one or more essential oils may be derivatized while other may be unaffected. Furthermore, exposure to light may be done either prior to the extraction of the essential oil components from their natural source or after their extraction.

According to the present invention, a mixture of at least one essential oil component or a derivative thereof obtained by irradiation of light with the emulsifier and the antioxidant may be directly added as an antimicrobial composition to foods, toiletries, and household articles for microbiocidal purposes. Also, the mixture may be prepared in the form of a liquid or as an aerosol by adding non-toxic bases in a suitable amount as needed, and are added or sprayed for microbiocidal purposes.

The concentration of the at least one essential oil component needed to achieve an effect can easily be determined by the artisan in each case and depends on the type of essential oil as well as on the manner of the application of the preparation. In the case of citral or geraniol, an effective amount ranges between about 0.1%-1%, particularly 0.2-0.4%.

The formulation may be applied to the produce to be protected at various times before and during their storage. When the formulation is applied to fruits, it will preferably be applied prior to packaging, e.g. after harvest. The formulation of the present invention may be applied to the produce by any method in which the produce will be contacted with an effective amount of the formulation, i.e. an amount that will inhibit its infection by microorganisms throughout the storage period. Examples for application methods are dipping, fungation, spraying and foaming the fruit in the packaging house. Another method could be by incorporating these materials inside a wax emulsion. In fact, as mentioned previously, the wax emulsion was a suitable solvent for treating several citrus fruits.

Another method of application is by fumigating the fruit in a relatively airtight chamber utilizing the volatility of many of the active materials such as citral.

Another possible method for application may be done by loading the active materials on a silica gel material used for drying agent or as an absorbent. This material could absorb more than 10% of its weight in our active materials and hold then as encapsulated entity. However, when the ambient humidity of this material rises then these active biocides are released and the water is replacing them. Indeed this is the situation when the fruit is enclosed in a storage room or in any container holding perishable agricultural produce that is continuously transpiring. Such an application could give a controlled slow release of the fungicide enabling longer protection from decay.

The formulation may also be applied via slow degradable polymers, which during their degradation release the essential oil compound contained within them onto the produce.

According to the present invention, the pH of the oil formulation is preferably acidic but may also be basic with a pH value up to 9.

As mentioned, the aqueous microbiocidal formulation should comprise a stabilizer for dissolving the at least one essential oil component. In case the stabilizer is ethanol it is shown that citral at a concentration of 0.2% was much more effective in inhibiting decay of non inoculated Washington orange fruit when applied as a formulation containing 10-50% Ethanol than when applied, at the same concentration, in an aqueous emulsion (Table 3, see also Example 4).

TABLE 3

Effects of citral and 50% ethanol on decay percentage of non-inoculated Washington oranges (Numbers = % of rotten fruit)

| Treatment | Months of Storage | | | | |
|---|---|---|---|---|---|
| | 0.5 | 1 | 2 | 3 | 4 |
| Non-treated | 5 | 8 | 20 | 29 | 36 |
| 0.2% Citral, 0.02% emulsifier in water | 0 | 8 | 28 | 35 | 48 |
| 50% ethanol in water | 0 | 4 | 14 | 20 | 23 |
| 0.2% Citral, 50% ethanol in water | 0 | 0 | 2 | 3 | 5 |
| Imazalil, 0.2% in water | 0 | 2 | 4 | 5 | 8 |

In addition, no marked damage to the produce, normally associated with essential oil application, occurs. In the presence of 10 to 50% ethanol the essential oil did not cause phytotoxic damage. The damage does not occur even when the essential oils are applied at relatively high concentrations (0.5 to 1%) known in the art to inflict considerable damage.

The effect of such formulations in reducing decay is thus demonstrated with all citrus fruits tested in the packinghouses (results shown in tables 3 and 4) and with mango and bell pepper fruits (data not shown). The experiment with bell pepper showed a good control of the major pathogens of pepper in Israel, *Botrytis cinerea* and *Alternaria alternata*.

TABLE 4

Effect of limonene exposed to three hours of sunlight on decay of kumquat fruit after storage for 11 days at 10° C. and shelf life simulation at 20° C. for 6 days.

| Treatment | End of storage |
|---|---|
| Water dip | 12.0 b |
| Ethanol 25% | 7.9 ab |
| Limonene[1] | 1.6 a |

[1]5000 µL L$^{-1}$ exposed to sunlight for 3 hours in 25% ethanol + 5000 µL L$^{-1}$ of TWEEN 20.

Figure 9:
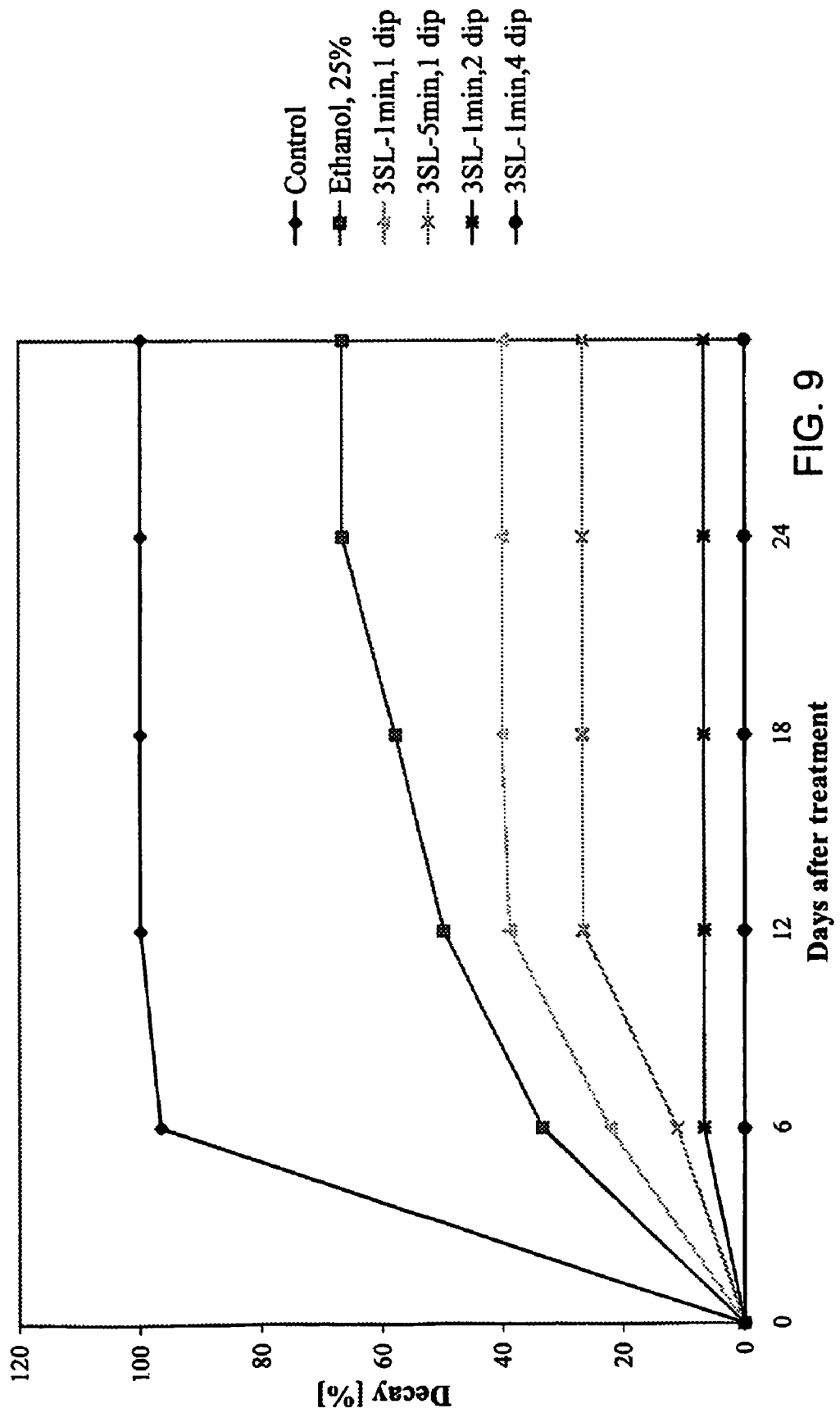
FIG. 9 shows the rate of decay of *Penicillium*-inoculated lemons treated with a 25% ethanol solution of 5000 ppm limonene exposed to sunlight for 3 hours. Effect of length of the dipping as well as the number of dips was compared.
Figure 10:
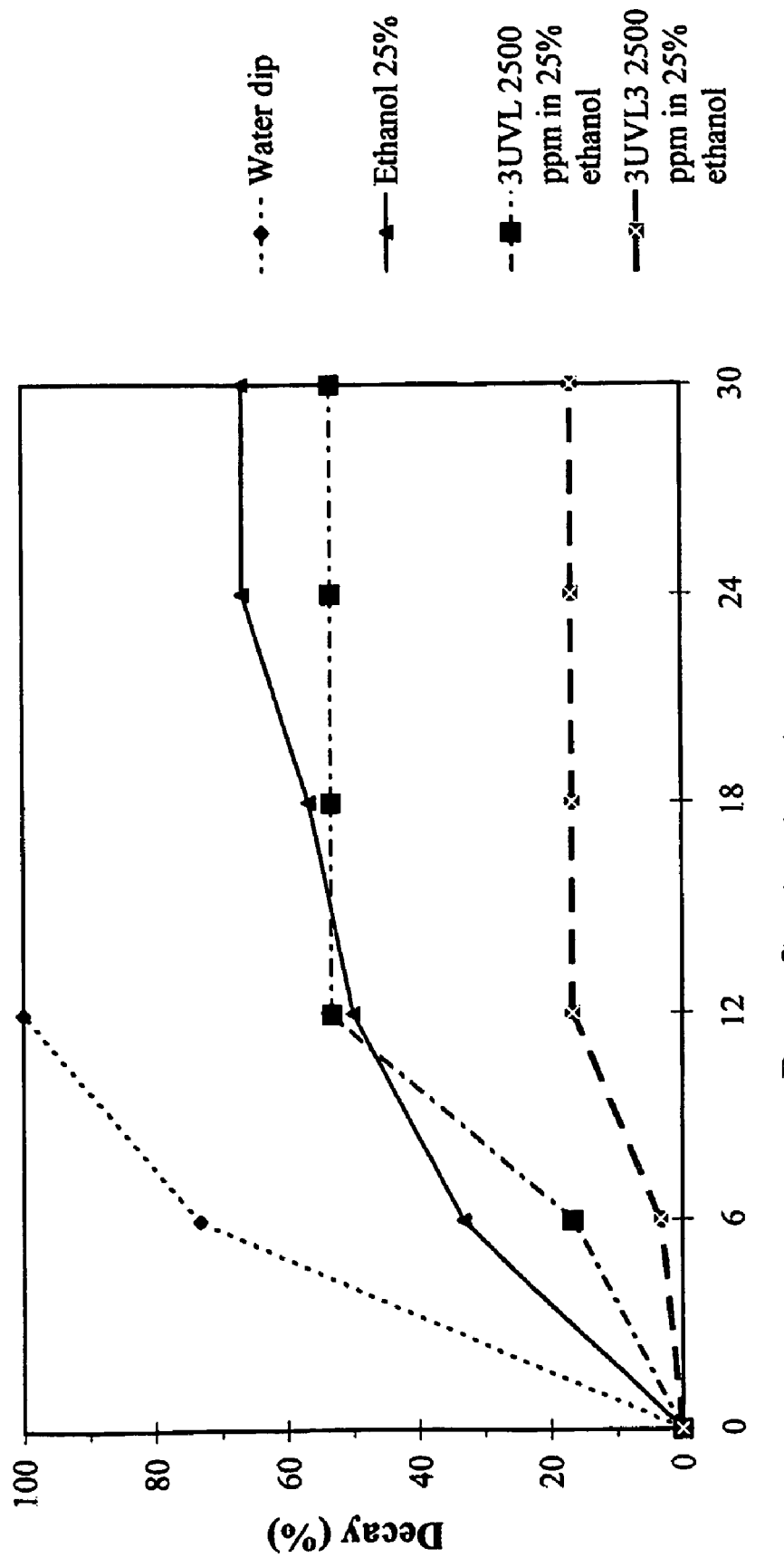
FIG. 10 shows the rate of decay of *Penicillium*-inoculated lemons treated with an aqueous solution of 2500 ppm limonene which, prior to its use, was UV irradiated for three hours and then dissolved in 25% ethanol. One minute dip treatment with this solution, (3UVL) was compared with three consecutive one minute dips in the same solution with one hour period between these dips (3UVL3). These treatments were compared with a dip in water or in 25% ethanol.

Quantitatively, the essential oil component, limonene, which belongs to the family of hydrocarbon monoterpenes, comprises about 85% of the essential oil components present in citrus. Limonene as such, however, is not adequately active. Notwithstanding the fact that it is not active it was found that limonene may serve as a precursor to a very active microbiocide by exposing homogenized fruit peel to sunlight followed by extraction of the oil with an organic solvent particularly by dichloromethane, hexane or ethylacetate. The same effect may be achieved by UV irradiation of limonene after its extraction (FIGS. 9 and 10). The same applies to synthetically produced limonene. Furthermore, limonene may also be oxidized using conventional oxidizing agents. One particular non-limiting example is heterogenous catalysis using molybdate salt.

Thus a microbiocidal according to the present invention may comprise limonene or a crude extract of essential oils comprising of a substantial amount of limonene that were irradiated by light. It should be noted that antioxidants should not be used when using such derivatives of essential oils that were exposed to irradiation of light.

Such an exposure of the limonene to irradiation leads to rapid photo-oxidation that forms a highly active antifungal material. Such a material may be characterized as the component that gives purple color in the vanillin-sulphuric acid test (hereinafter "vanillin test") or preferably by blue fluorescence obtained as a result of irradiation by a UV lamp. Although this test may react with other terpenes and their derivative compounds the specific product of limonene may be characterized by its typical color and its retention ratio,— $R_f$ on the chromatogram. Photo-oxidation may be done by either exposure of the limonene to ultraviolet or white light or by its exposure to sunlight. In these three cases the obtained material had the same retention time in HPLC. These materials gave the same purple color in the vanillin test and the same spot on a thin layer chromatogram plate. It thus may be concluded that all these paths of exposure result in the same material. It was found that chlorophyll participates in the photo-oxidation of limonene to the new product that gives the positive purple color response in the vanillin test. This material showed a high antifungal activity in the bioassay of inhibition of elongation of conidia of *Penicillium digitatum*. The resulting activity was much higher than that of scoparone or scopoletin, materials known as endogenous phytoalexins of citrus fruits, or than that of citral which was known as the most active constitutive antifungal material in lemon fruit (Ben Yehoshua et al, 1992)

Another observation showed that this material induces the resistance mechanisms of the citrus fruit, such as the elicitation of the accumulation of phytoalexins (FIG. 1). Treating uninoculated lemons by injecting 5 µl photo-oxidized limonene into the albedo tissue, just below the flavedo, elicited in these lemons the production of scoparone and scopoletin up to levels adequate to protect the fruit from the pathogen.

Figure 2:
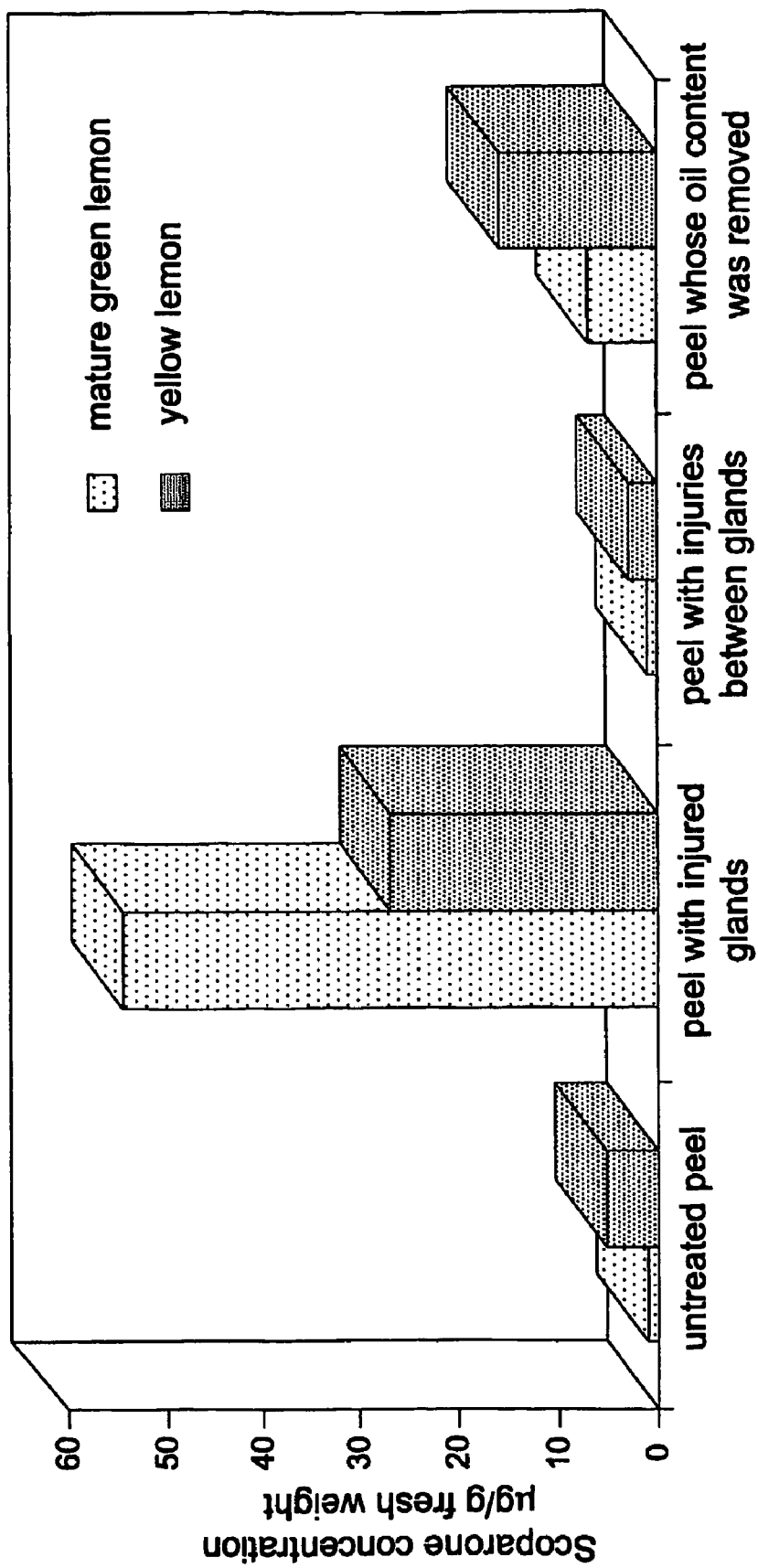
FIG. 2 shows the effect of fruit maturity of lemons on the production of phytoalexins in mature green and yellow lemon fruits.
Figure 7:
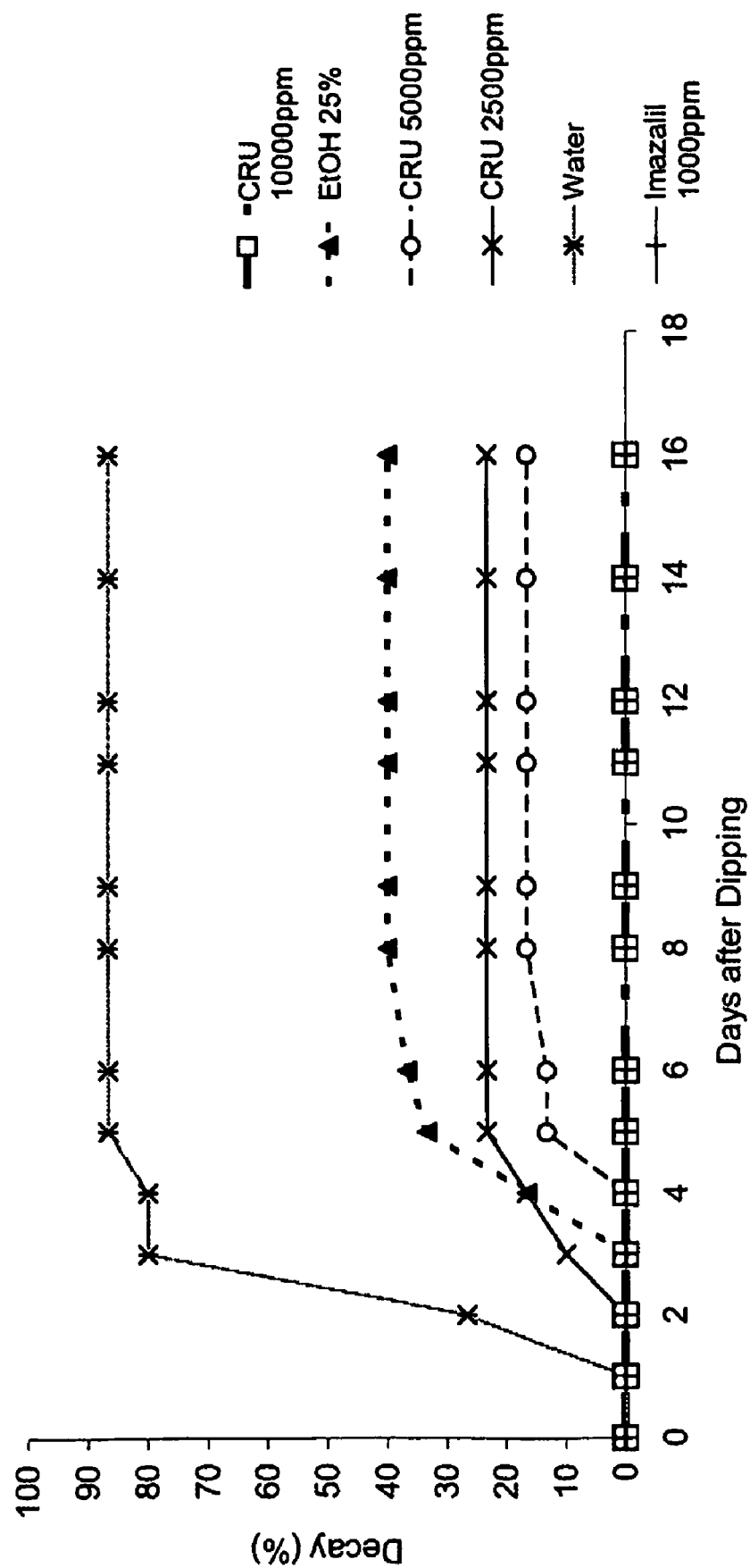
FIG. 7 shows the rate of decay of *Penicillium*-inoculated lemons treated with a 25% ethanol aqueous emulsion of dichloromethane crude extract of green lemon flavedo in comparison with imazalil 1000 ppm and 25% ethanol solution.

Similar results were achieved by injecting the dichloromethane or hexane crude extract of lemon flavedo that was shown to prevent decay completely (FIG. 7). Similarly injuring the oil glands or injecting limonene into albedo tissue of mature green lemons resulted in a very important effect of eliciting the endogenous resistance mechanisms of citrus fruits as shown by the accumulation of scoparone in FIG. 1. Such injury of yellow fruit gave much lower response showing that the maturity of fruit affects this resistance response and older fruit is less protected (FIG. 2). In fact, this lower resistance of yellow fruit was seen in many other experiments. Interestingly injecting citral did not elicit the same protective response (FIG. 1). Probably the citral injection unlike the limonene did not induce the production of the vanillin positive active material. Furthermore much higher levels of both scoparone (over 1000 µg/g fresh weight) and of scopoletin (over 200 µg/g fresh weight) were found after dipping inoculated fruit in the crude dichloromethane extract that prevented decay (FIG. 7). The phytoalexins level found was several fold of the amount required to control completely the pathogens. Thus apparently, the formed limonene hydroperoxides form reactive oxygen species, which elicit the immune system of the plant. Such reactive oxygen species effect the pathogen as well. These reactive oxygen species have a short life and decompose well before the fruit is distributed to the market.

An important aspect of this new invention is that the decay control of the pathogen is achieved by both a direct inhibition of the pathogen as well as by eliciting the endogenous mechanisms of the plant resistance. Thus, sun or UV-treated limonene or the sun treated crude extract exerts both direct antifungal activity as well as elicitation of the endogenous resistance.

Figure 11:
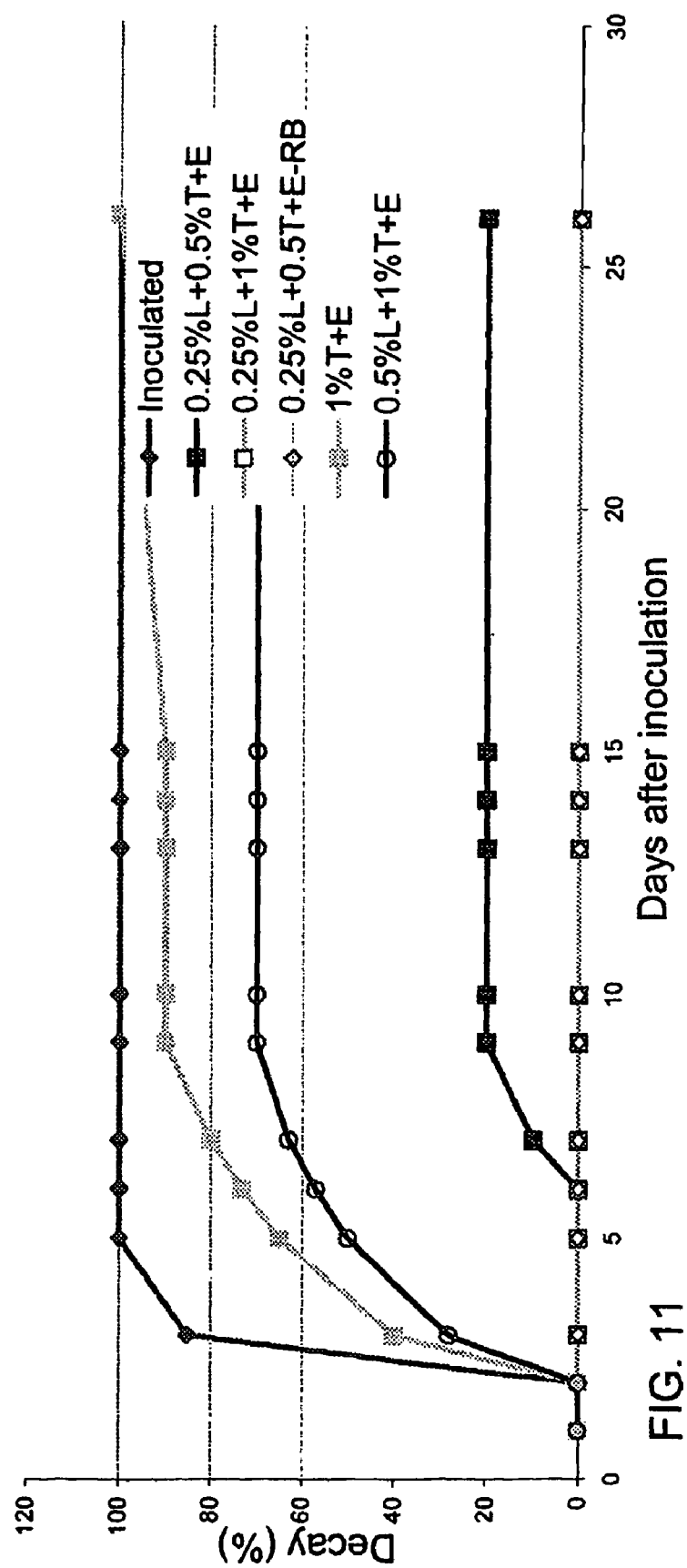
FIG. 11 Shows the effect of limonene hydroperoxide prepared by photooxidation with Rose Bengal on decay percentage of lemon fruit inoculated with *Penicillium digitatum*.

It was previously reported, without any relevance to the antifungal activity, (Schieberle, P., Maier, W., Firl, J. and Grosch, W. 1987, HRGC separation of hydroperoxides formed during the photosensitized oxidation of (R)-(+)-limonene. J. of High Resolution Chromatography & Chromatography Communications p. 588) that irradiating limonene produces various peroxides. It is now shown that the formed hydropeoxides, and in particular, (1S,4R)-p-*mentha*-2,8-diene 1-hydroperoxide; (1R,4R)-p-*mentha*-2,8-diene 1-hydroperoxide; (2R,4R)-p-*mentha*-6,8-diene 2-hydroperoxide; and (2S,4R)-p-*mentha*-6,8-diene 2-hydroperoxide may be used as effective biocides in the aqueous solution of the present invention. The presence of these hydroperoxides in the irradiated limonene of the present invention was confirmed by gas chromatography mass spectrometry and Nuclear Magnetic Resonance studies (data not shown). In the present invention a novel procedure giving high concentrations of hydroperoxides was developed with the Rose Bengal as the catalyst or activator that raised the oxygen in the reaction to the energy level of singlet oxygen. Utilizing this procedure results in nearly all limonene being converted to the hydroperoxides. The mixture of these hydroperoxides was very effective in controlling decay of inoculated lemons even at the dosage of 2500 ppm (FIG. 11).

Experiments done clearly show that if the crude extraction of the peel or if the extracted limonene was not irradiated or exposed to sunlight, the resulting limonene solution was indeed not adequately active and too variable for inhibition of decay. The decay in such cases developed as if the fruit was not contacted with a microbiocidal formulation at all. Thus the antifungal activity as well as the induction of the resistance mechanisms as shown by the accumulation of the scoparone is related to these hydroperoxides of limonene.

Exposure to sunlight or irradiation of the dichloromethane or hexane extract of lemon flavedo should be conducted for 3 to 6 hours. The efficiency of the extract hydroperoxide formulation as a biocidal composition grows with longer periods of exposure of the fruit to the hydroperoxide solution. Dipping inoculated fruit in a hydroperoxide solution (limonene exposed to 4 hours of sunlight) for four consecutive periods of 1 minute each resulted in the prevention of decay of inoculated lemons kept at 20° C. for a period of over three weeks (FIG. 9). The effect of exposure of limonene to 3 hours of sunlight and its efficiency as preventing decay compared to no treatment (dipping in water) or treatment with an ethanol solution (25%) are summarized in Table 4 in a commercial like experiment with uninoculated fruit. Furthermore an orchard spray with 5000, 10,000 or 20,000 ppm aqueous formulation of limonene in 25% ethanol solution that had been fully converted, induced production of scoparone and scopoletin in Valencia fruit on (and off) the tree, reduced decay of this fruit when inoculated with *P. digitatum* after harvest (data not presented).

In a separate experiment both citral and sun treated limonene (dissolved in 25% ethanol) showed a marked inhibition of another pathogen *Cladosporium herbarum* growing on inoculated corn cob.

The conventional method of controlling decay in citrus packinghouses comprises several compounds that are also environmentally friendly, but are not included in the present formulation for technical reasons. Such compounds are calcium salts, gibberelic acid, 2,4-dichloroacetic acid acetaldehyde, chitosan or chitosan plus low concentration of metals such as Zn or Cu, some organic acids such as acetic acid, propionic acid etc. These compounds might be part of our environmentally friendly new formulation. In fact recent data demonstrated such an activity. In fact lowering the pH of the formulations down to 2 or 3 helped also the control of the pathogen in inoculated fruit experiments.

The invention will now be illustrated in more detail in the following non-limiting examples with occasional reference to the annexed drawings.

EXAMPLES

Example 1

Minimum Inhibitory Concentration against *P. digitatum* and Mode of action of essential oils as compared to imazalil.

The minimum inhibitory concentration (MIC) of over 50 compounds that were found in the oil glands of citrus fruits was evaluated (in vitro) by establishing the lowest concentration of the compound where no growth of the pathogen occurred (in vitro) in Petri dishes. Table 5 gives the MIC of the more promising compounds (as compared to imazalil). The requisite amount of each of the compounds to be tested, dissolved in 0.5 ml acetone, was added to a sterile Petri dish (90 mm) containing 15 ml of molten potato dextrose agar (PDA) (50° C.) to give a final concentration of 1 mg ml$^{-1}$. The dish was gently agitated to ensure an even distribution of the test compound and the agar was then left to set. The dishes were inoculated using a mycelial disc (8 mm) cut from an agar plate culture of *P. digitatum* which had not yet begun sporulation. The mycelial discs were placed in the center of each test dish and then put at 24° C. Fungal inhibition was monitored by measuring the diameter of hyphal growth after 7 days.

A further test was made (in vitro) to investigate whether the mode of action was fungicidal or fungistatic; the mycelial disc of inoculum from the assay plate was transferred to a plate containing just PDA. Plates were then monitored for growth over the next 5 days. If growth resumed, the compound was classified fungistatic, and if growth was not resumed it was classified as fungicidal. The results are shown in Tables 5 and 6.

TABLE 5

Minimum Inhibitory Concentration (MIC) against *P. digitatum* and Modes of Action

| Test Compound | MIC mg ml$^{-1}$ agar | Mode of action |
|---|---|---|
| Imazalil | <0.025 | Fungicidal |
| Decanol | 0.05 | Fungistatic |
| Octanol | 0.1 | Fungicidal |
| Nonanol | 0.2 | Fungistatic |
| Citral | 0.4 | Fungicidal |
| Cinnamaldehyde | 0.4 | Fungicidal |
| Perillaldehyde | 0.4 | Fungicidal |
| Perillalcohol | 0.4 | Fungicidal |
| Citronellal | 0.6 | Fungistatic |
| Terpineol | 0.8 | Fungicidal |
| Carveol | 1.0 | Fungistatic |

TABLE 6

Inhibitory Effects of Various Compounds against 3 different species of Citrus Pathogens in the In Vitro Agar Diffusion Assay.
GROWTH INHIBITION AREA OF THE PATHOGEN[1] (cm$^2$)

| Compound | *Geotrichum Candidum* | *Penicillium italicum* | *Alternaria citri* |
|---|---|---|---|
| Imazalil | 8.3 | Total inhibition | 42.8 |
| Cinnamaldehyde | 24.2 | Total inhibition | Total inhibition |
| Octanal | 3.6 | 2.6 | 5.3 |
| Decanol | 0.95 | Total inhibition | Total inhibition |
| 1-Octanol | Total inhibition | Total inhibition | Total inhibition |
| Perillaldehyde | Total inhibition | Total inhibition | Total inhibition |
| Citral | 10.6 | Total inhibition | Total inhibition |

[1]Total inhibition is the maximal inhibition which is 62.3 cm$^2$

Agar Diffusion Assay Method

Potato dextrose agar (Difco) was prepared and sterilized. The medium was then cooled in a water bath to 50° C. prior to inoculation by the addition of a suspension of *P. digitatum* spores in sterile water, to make the final concentration of spores in the medium at 10$^4$ spores/ml. The medium was gently mixed to disperse spores evenly prior to dispensing 15 ml into each 90 mm diameter Petri dish. Five mg of each substance to be tested were pipetted into a sterile 13 mm antibiotic Whatman assay—paper—disc which was placed centrally on the inoculated agar plate. Plates were incubated at 24° C. for 3 days. Antifungal activity was monitored by measuring the width of the clear zone from the edge of the paper disc to the area of fungal growth. Values are for the radius (mm) of the zone of inhibited growth of the pathogen on the Petri dish. Total inhibition means that growth was completely inhibited.

In other experiments (data not shown) it was found that citral and other essential oils formulations were effective in controlling growth of the fungi *P. digitatum* and of the bacteria *Erwinia carotovora*, a major pathogen of agricultural produce.

Example 2

Unblemished grapefruit were harvested from the orchard and on the same day sorted again in the laboratory to eliminate injured fruit. The grapefruit were washed with tap water and air-dried. Each fruit was then inoculated by piercing its flavedo tissue 1.5 mm deep with a tool incorporating three needles at three different sites. Prior to each piercing, the tool was immersed in a spore suspension of *Penicillium digitatum* (10$^6$ spores/ml). The inoculated grapefruit were kept at 17° C. and 85% relative humidity for 24 hours after which the grapefruit were divided into six groups and grapefruit from each group were treated by dipping for two minutes in: (a) water; (b) 25% Ethanol (EtOH); (c) 0.2% Geraniol in 25% EtOH; (d) 0.1% Citral in 25% EtOH, (e) 0.2% Citral in 25% EtOH and (f) 0.5% Citral in 25% EtOH.

Figure 3:
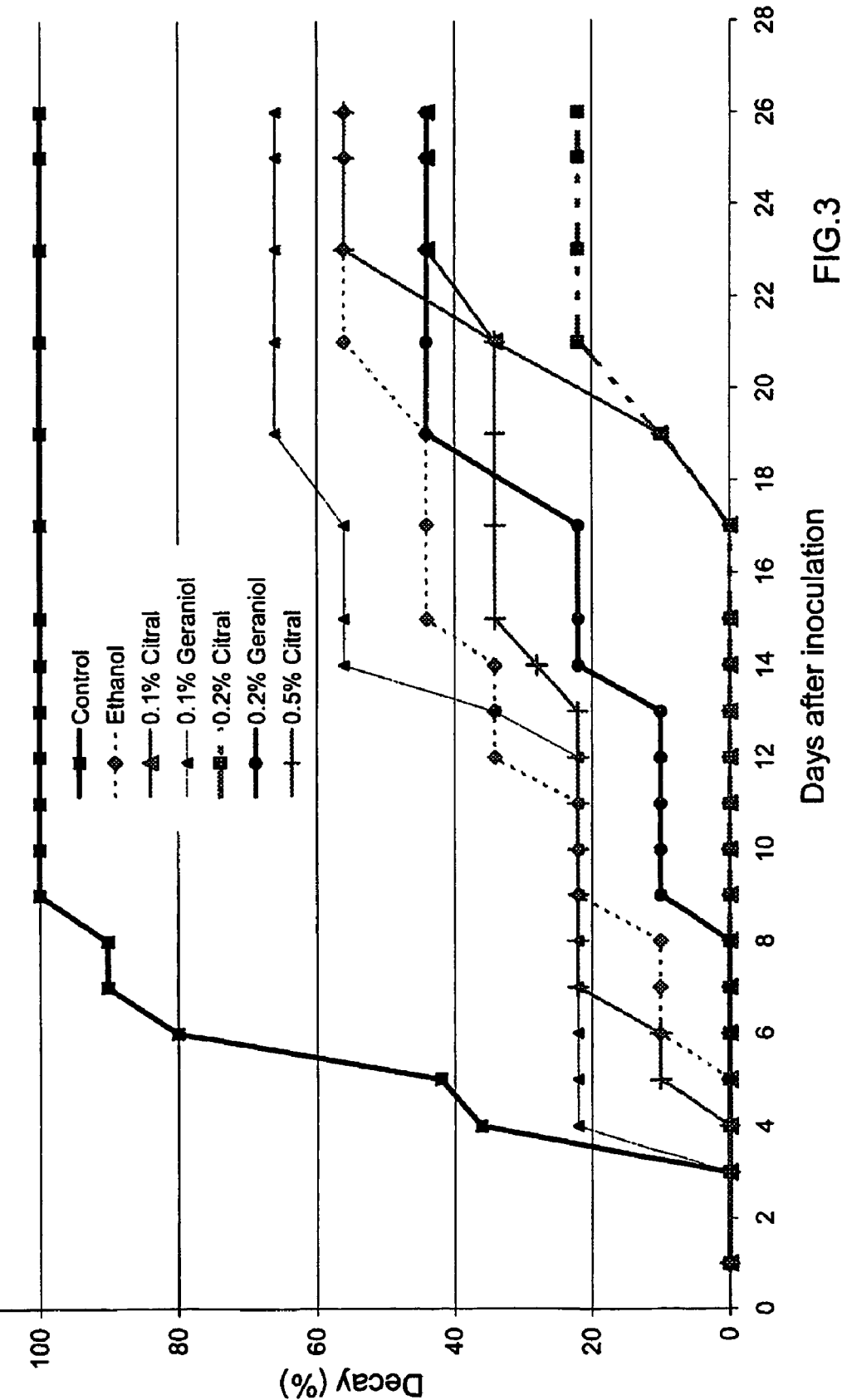
FIG. 3 shows the rate of decay of *Penicillium*-inoculated grapefruit treated by dipping in formulations of citral, and geraniol.

The percentage of rotten fruit in each group was measured on each day after treatment and the results are shown in FIG. 3.

As seen in FIG. 3, control fruit (dipped in water only) developed decay rapidly reaching 100% eight days after inoculation. Decay of fruit dipped in 25% Ethanol (EtOH) was delayed, but 6 days after inoculation a rapid rise in decay of the EtOH treated fruit began and three weeks after inoculation more than 50% of the fruit were rotten.

In contrast, fruit dipped in 0.2% Geraniol and 0.1-0.2% Citral dissolved in 25% EtOH showed a lower rate of decay and on the 18$^{th}$ day after inoculation only 20-40% of the fruit in these groups were rotten. The most efficient inhibition of decay resulted from dipping of inoculated fruit in 0.2% Citral dissolved in 25% EtOH which completely inhibited decay of fruit until 18 days after inoculation and resulted in only 20% of the fruit showing decay as late as 28 days after inoculation. The dose of 0.5% citral was too high and in this experiment enhanced decay due to phytotoxicity.

Example 3

Figure 4:
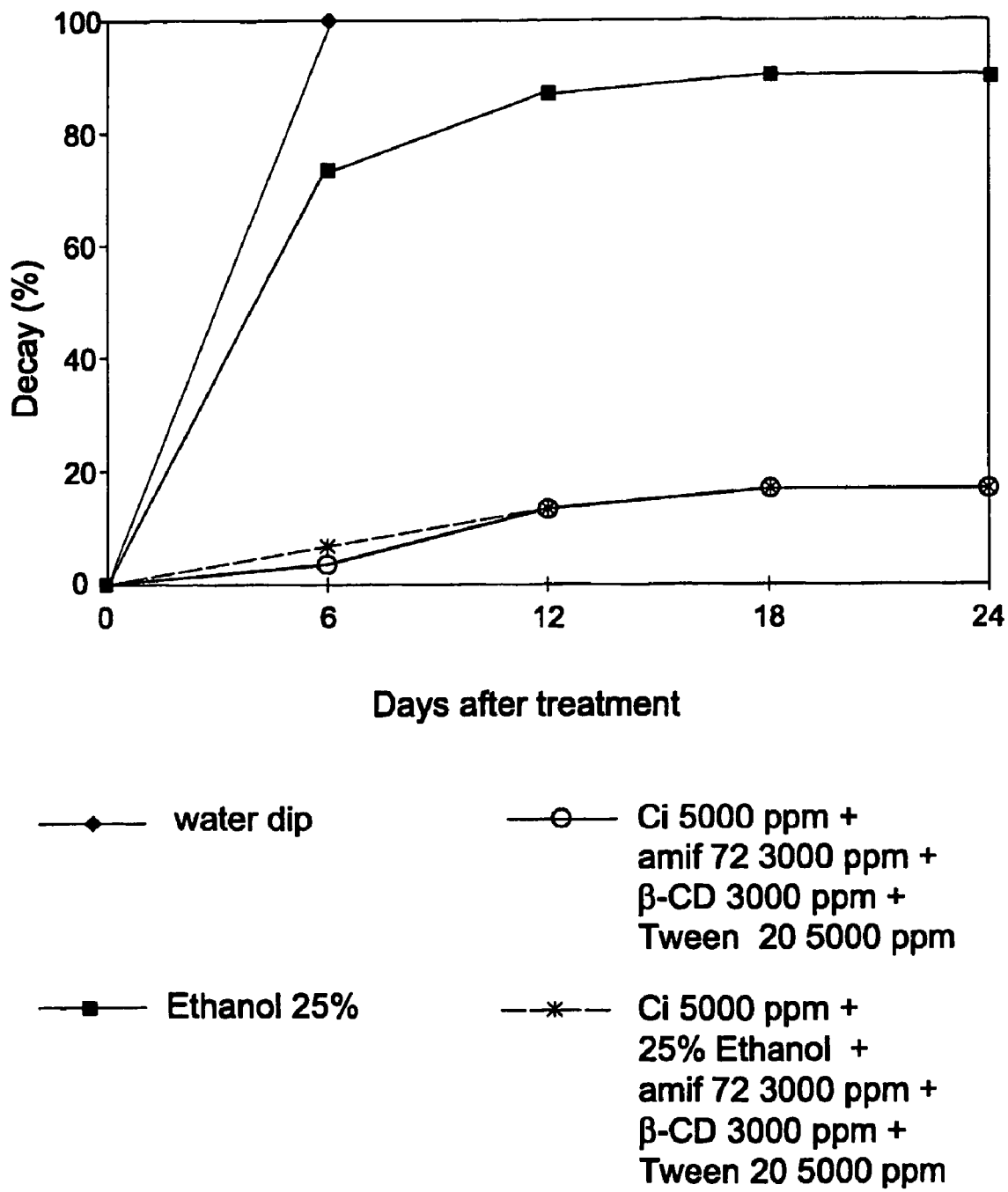
FIG. 4 shows the rate of decay of *Penicillium*-inoculated lemons treated with an aqueous emulsion of citral stabilized by 25% ethanol, amif 72 (20% of butylated hydroxyanisole, 6% of propyl gallate, and 4% of citric acid in propylene glycol), β-cyclodextrin and polyoxyethylene sorbitan monolaurate (Tween 20) as compared to the decay of fruit of the same kind with 5000 ppm of Tween 20 without ethanol.

Lemons were inoculated as shown in Example 2 and treated with and without 25% of ethanol to check whether the 5000 ppm of the emulsifier Tween 20 could stabilize the antifungal activity of citral. Results, shown in FIG. 4, demonstrate that this concentration of Tween 20 enhanced the activity of citral. Additionally it prevented the phytotoxicity that is usually caused by citral if not dissolved by ethanol. Probably the emulsifier enables the formation of a microcolloidal stable emulsion, which prevents the phytotxicity by allowing uniform dispersion of citral, which is phytotoxic by itself in these concentrations. Thus, Tween 20 combined with the antioxidant BHA could substitute for the ethanol in the formulation.

Example 4

Non-inoculated Washington navel oranges were divided into four groups which were treated as follows: (a) no treatment; (b) dipped in 50% Ethanol; (c) dipped in 0.2% Citral in 0.02% L-77 Emulsifier (aqueous emulsion); (d) dipped in 0.2% Citral in 50% Ethanol; and (e) dipped in a 0.2% aqueous Imazalil solution.

Oranges were then stored for four months at 15° C. in 50-75% relative humidity and the percentage of rotten fruit in each group was measured at different time periods after storage. The results are shown in Table 3.

As can be seen in Table 3, the percentage of rotten fruit following treatment with the inventive formulation (0.2% citral in 50% ethanol) was significantly lower than that of the treatment with either citral in an aqueous emulsion or with ethanol alone. Furthermore, the results with the invention formulation are comparable with those achieved with imazalil. The high decay level in the citral treatment with the 0.02% emulsifier was probably caused by the phytotoxicity that was seen in this treatment due to the lack of either ethanol or higher level of emulsifier.

Example 5

Meat cuts of beef were divided into the following two groups: (a) non-treated meat cuts; (b) meat cuts dipped for 30 seconds in 0.2% Citral dissolved in 20% ethanol. The meat cuts were then stored in 1° C. and 85% relative humidity and a total count of the microbial population in each meat cut was carried out 2 weeks after treatment. The results showed that the total counts of microbial population in the meat cuts treated by the citral dissolved in 20% Ethanol was less than 10% of the total count found in the non-treated meat cuts.

Example 6

Figure 5:
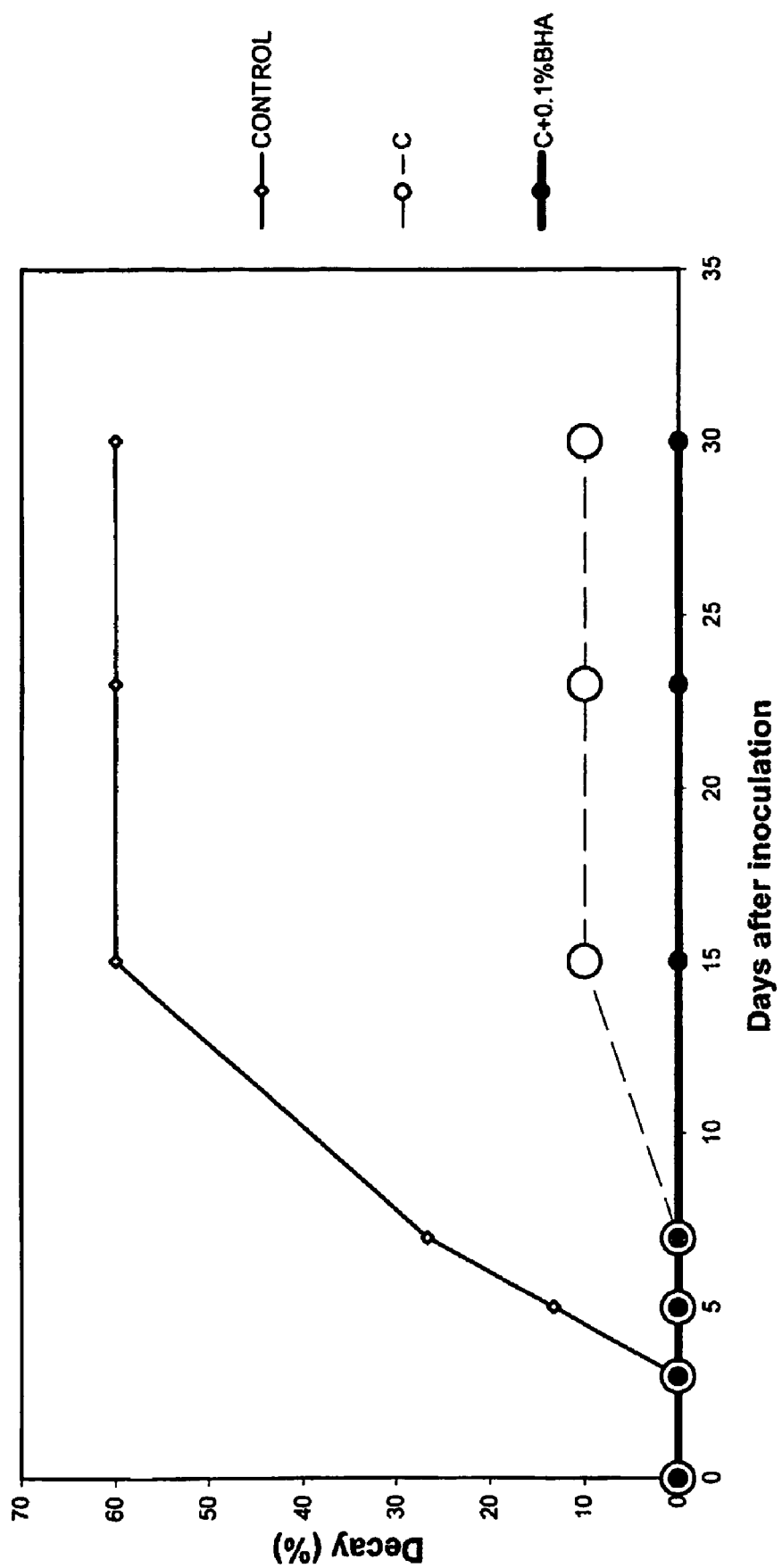
FIG. 5 shows the rate of decay of *Penicillium*-inoculated lemons treated with an aqueous emulsion of citral comprising octyl-phenyl polyether alcohol (Triton is X100) and butylated hydroxyanisole (BHA).

Lemons inoculated with *Penicillium* as shown in Example 2 were dipped for 2 minutes in an aqueous solution comprising citral, emulsifier (Triton X100) and BHA at various concentrations. The concentration of Citral is 1.0%. The control solution was comprised of 0.5% Triton X100. The results are shown in FIG. 5. The effect of 0.1% BHA in enhancing the activity of citral in preventing the development of the pathogen is clearly shown.

Example 7

Figure 6:
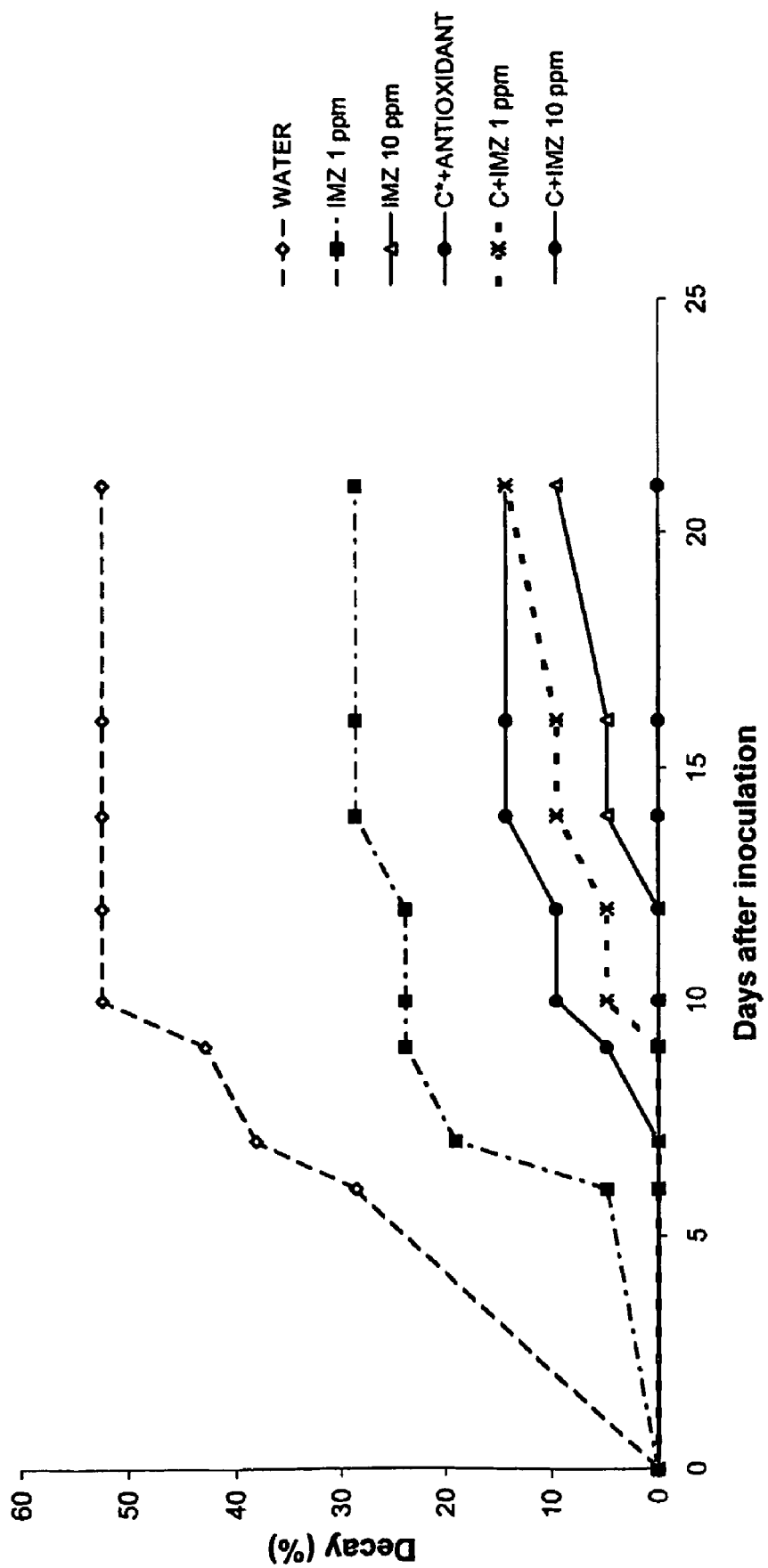
FIG. 6 shows the rate of decay of *Penicillium*-inoculated lemons treated with an aqueous emulsion of citral comprising polyoxyethylene sorbitan monolaurate (Tween 20) and butylated hydroxyanisole (BHA) compared to the rate of decay where imazalil is added. (Imazalil is a fungicide, which is commonly used in the post harvest protection of fruits and vegetables).

Lemons inoculated with *Penicillium* as shown in Example 2 were treated with an aqueous solution comprising 0.5% Citral, 0.3% BHA, Tween 20 and imazalil and stored at 20° C. for a period of 21 days. The results are shown in FIG. 6. Imazalil concentrations of 1 and 10 ppm were insufficient to control completely decay. However the addition of 0.5% citral to the 10 ppm imazalil prevented decay completely and enabled reducing both the dosage and residues of this effective, but undesirable, synthetic fungicide. Addition of citral to 1 ppm imazalil did not control decay adequately, but was much better than 1 ppm imazalil by itself.

Example 8

Lemons inoculated with *Penicillium* $10^4$ spores/ml were dipped a day later in an aqueous solution comprising citral and a detergent (Tween 20), other essential oils as well as some combination of the more effective essential oils and kept for a period of six days. The results of microbial protection achieved with these various essential oils are shown in Table 7. Some of these essential oils, particularly cinnamic acid, vanillin, octanol and mixture of several essential oils, were more effective in these experiments than citral. Additionally their activity against *P. digitatum* lasted longer.

TABLE 7

Effect of various essential oils on percentage decay of inoculated fruit kept 6 days at 20° C.

| No. | TREATMENT | % Decay |
|---|---|---|
| 1. | Water dip | 73 |
| 2. | Ethanol 25% | 30 |
| 3. | 1-octanol 5000 ppm + EtOH 25% + Tween 20 5000 ppm | 7 |
| 4 | Citral 1000 ppm + 1-nonanol 1000 ppm + 1-octanol 1000 ppm + Carveol 1000 ppm + EtOH 25% + Tween 20 4000 ppm | 7 |
| 5. | Trans-cinnamic acid 2500 ppm + EtOH 25% + Tween 20 2500 ppm | 3 |
| 6. | 1-octanol 2500 ppm + EtOH 25% + Tween 20 2500 ppm | 10 |
| 7. | Benzaldehyde 2500 ppm + EtOH 25% + Tween 20 2500 ppm | 20 |
| 8. | Citral 2500 ppm + EtOH 25% + Tween 20 2500 ppm | 13 |
| 9. | Vanillin 2500 ppm + EtOH 25% + Tween 20 2500 ppm | 7 |
| 10. | Carveol 2500 ppm + EtOH 25% + Tween 20 2500 ppm | 23 |

Example 9

General Procedure for Obtaining a Most Active Crude Extract From Lemon Flavedo.

Lemon fruit flavedo (exocarp) was taken and extracted overnight in dichloromethane, then exposed to sunlight for about 18 hours until the color of the dichloromethane extract turned brown. The flavedo was blended and filtered through a layer of Whatman paper. The extracted solution was evaporated to remove the dichloromethane and the dense liquor was further separated by chromatography with a silica 60 column using dichloromethane as a carrier. Two fractions of dichloromethane, one green and the other colorless, were obtained after chromatography. The crude active extract was isolated by evaporation of the green dichloromethane fraction. Lemon fruit inoculated with *Penicillium digitatum* $10^4$ spores/ml were dipped 24 h after inoculation in an ethanolic solution comprising of the extracted vanillin-positive compounds and then kept at 20° C. Effect of the compounds on pathogen development on the fruit was checked daily during storage. The effect is shown in FIG. 7, for various concentrations (10,000, 5000 and 2,500 ppm of crude extract) compared to the effect achieved by an ethanol solution, imazalil or water. The 10,000 ppm crude extract completely prevented the development of the pathogen. In such a high dose of the crude extract, some fruit showed some phytotoxicity. However it was shown that this phytotoxicity was mainly caused by different components and not by the active antifungal components since the phytotoxicity could be removed while the biocidal activity maintained.

Similar results were achieved by hexane extractions of the limonene.

Example 10

Limonene-hydroperoxides were prepared by the following two routes from limonene.

Route 1: By photooxidation: The conversion of limonene and the yield of the reaction was nearly 100% after approximately 8 hours reaction time. Pure EtOH was used as a solvent, Rose Bengal as activator. Other light activators, for example chlorophyll, also catalyze the reaction. High-pressure mercury lamp with WG 345 filter was used for the photo catalytic reaction. Other ways of light excitation, like monochromatic light (light emittance≈345 nm in the case of Rose Bengal), UV light, laser also give limonene-hydroperoxide product.

Route 2: Via a heterogenous catalytic route (no light): Sodium Molybdate ($Na_2MoO_4 2H_2O$) was used as a catalyst, 300 ml concentrated $H_2O_2$ as an oxidation agent was added to the solvent, to 700 ml EtOH. The reaction conditions to get the desired products were: atmospheric pressure, 50° C. temperature and 5-6 hours reaction time with continuous stirring. The conversion of limonene and the yield of the reaction was nearly 100%.

Figure 12:
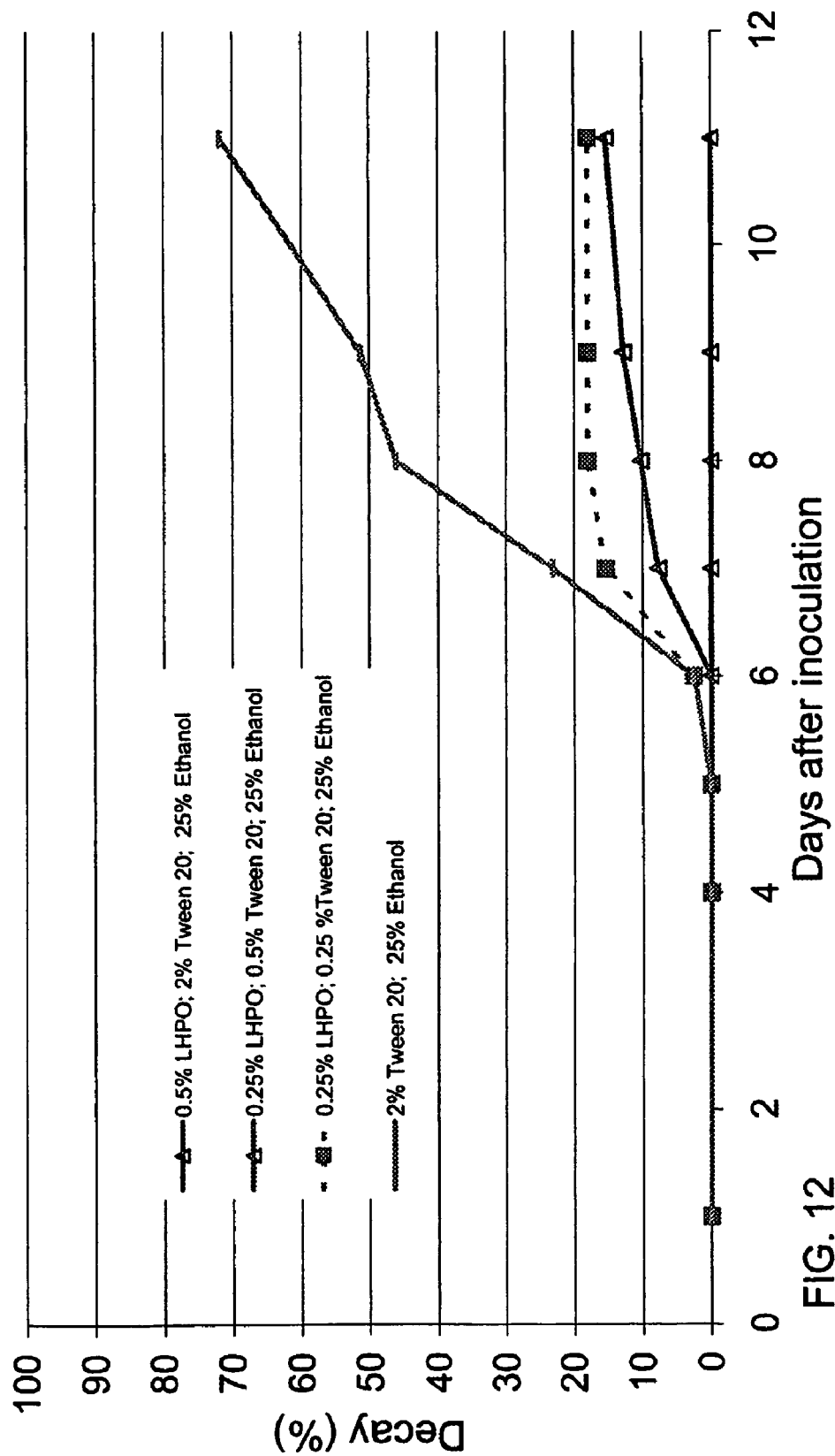
FIG. 12 Shows the effect of limonene hydroxyperoxide prepared with a molybdate catalyst on decay of lemon fruit inoculated with *Penicillium digitatum*.
Figure 13:
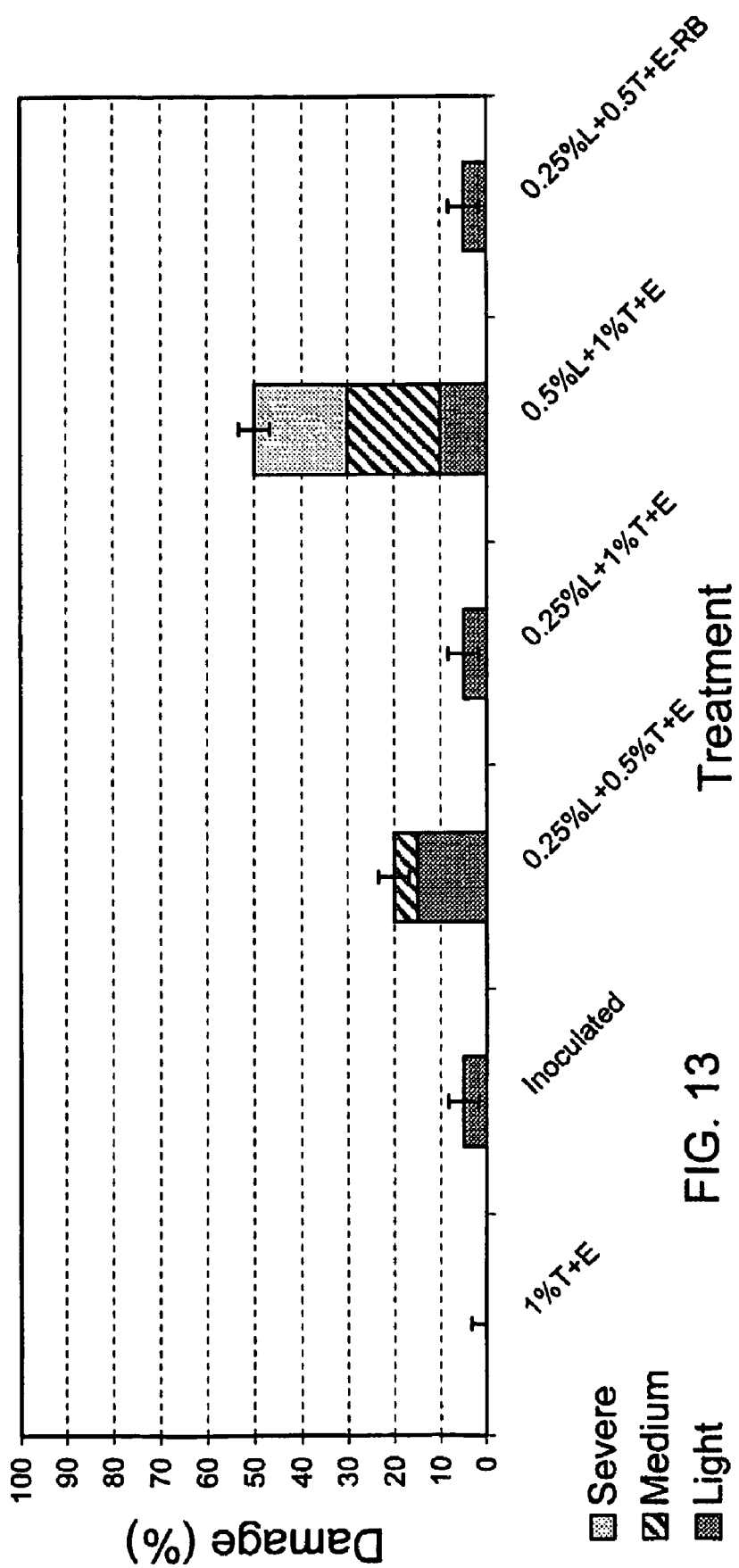
FIG. 13 Shows the effect of removal of the Rose Bengal catalyst and the dosage of Tween 20 on the phytotoxicity of lemon fruit treated with limonene hydroxyperoxide.

The products of the two routes were compared. Gas chromatography measurements showed approximately similar product distributions. The antifungal activity of the products prepared in the two different routes was checked in the same method. Lemons inoculated with *Penicillium* ($10^4$ spores/ml) were dipped in an aqueous solution comprising limonene-hydroperoxide, a detergent (Tween 20), and ethanol. Decay was evaluated at specific intervals during a period of 26 days. The results of microbial protection achieved with these mixtures are shown in FIGS. 11 and 12.

In the case of Route 1, phytotoxicity of the fruit took place after the dipping. Increasing the amount of Tween 20 in the mixture and removing the Rose Bengal eliminated or at least markedly reduced this phytotoxicity. The Rose Bengal was separated from the active hydroperoxide by mounting the solution on Silica column using a hexane:ethyl-acetate 9:1 mixture. After the removal of the Rose Bengal very little if any phytotoxic damage was found.

The formulation used comprises 0.25% limonene-hydroperoxide, 1% Tween 20, 400 ppm Rose Bengal and 25% EtOH. Such a composition, completely inhibited decay development, without any phytotoxicity. Sixty days after inoculation no decay was found on the treated fruit while in the sample used as control, inoculated fruit rotted after 5 days (FIG. 11). This antifungal effect can be explained both by the direct antifungal effect of the limonene hydroperoxide and also the increased level of scoparone and scopoletin that was induced by the limonene-hydroperoxideas shown previously for sun-treated limonene (FIG. 1).

In the case of the Route 2, the formulation used comprised 0.5% and 0.25% limonene-hydroperoxide, 2% Tween 20 and 25% EtOH. Decay of inoculated lemons did not develop during 12 days (FIG. 12). The dose of 0.5% LHPO gave complete control of decay and 0.25% LHPO had still some decay developed. The control solution, comprising 2% Tween 20 and 25% EtOH exhibited very low antifungal activity (90% decay) showing again that the active compound is the limonene-hydroperoxide.

Route 2 is preferred, in view of the fact that the Rose Bengal, which was used as a catalyst in Route 1, had undesirable effects: it reduces the antifungal activity and enhances the phytotoxicity, and at the end of the reaction it must be removed from the active compound.

Example 11

Lemons inoculated with *Penicillium* ($10^4$ spores/ml) were dipped in an aqueous solution comprising citral, a detergent (Tween 20), other essential oil components as well as a dichloromethane crude extract of lemon flavedo exposed to sunlight. Decay was evaluated at specific intervals during a period of 20 days. The results of microbial protection achieved with these various essential oils are shown in FIG. 8.

Figure 8:
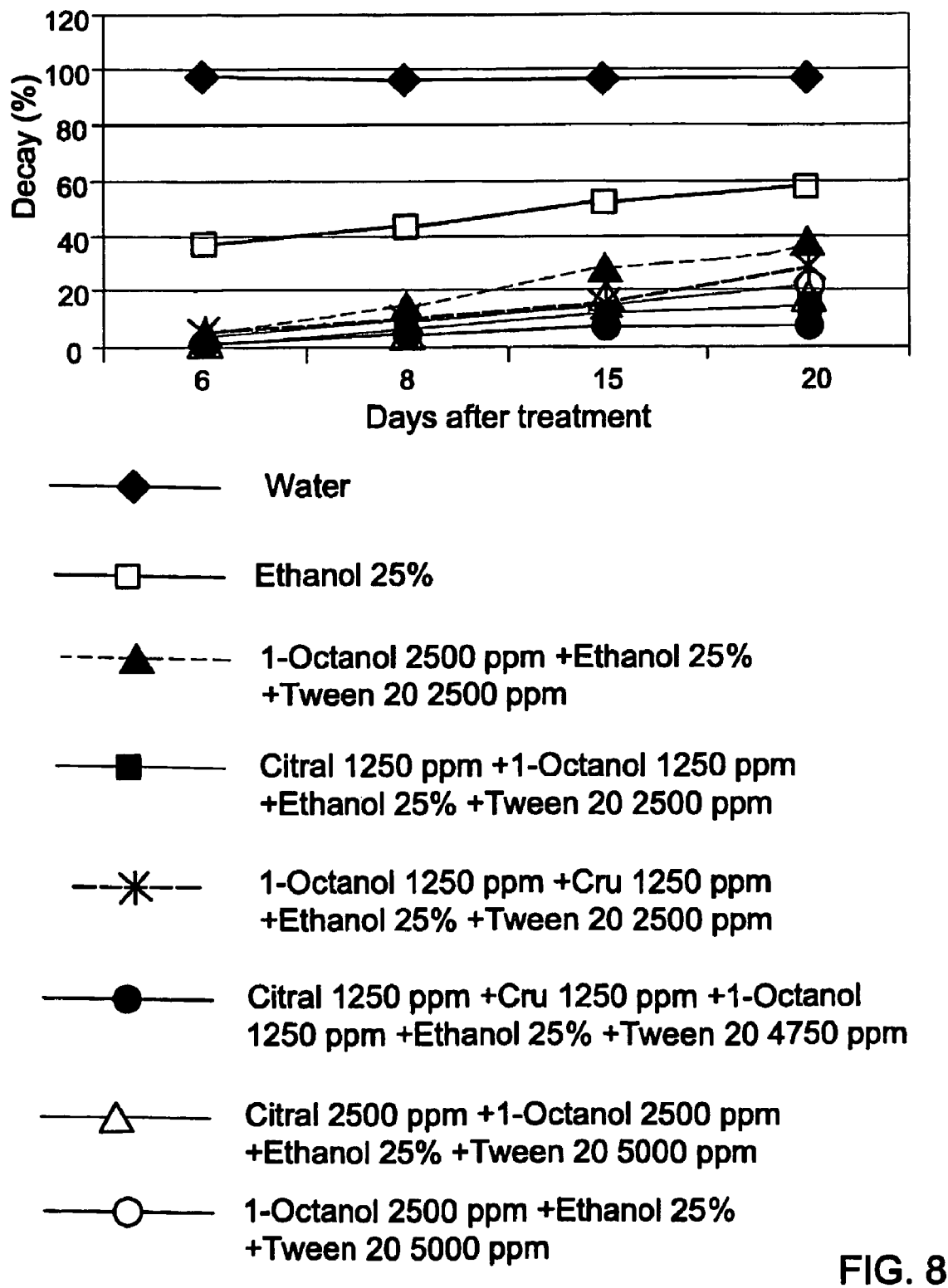
FIG. 8 shows the rate of decay of *Penicillium*-inoculated lemons treated with a 25% ethanol aqueous solution of various combined formulations comprising citral, 1-octanol and dichloromethane crude extract in 25% ethanol from lemon flavedo that, prior to its use, was exposed to sunlight for 4 h.

The combination of sun-treated crude, citral and 1-octanol at concentration of 0.5% and 0.25%, respectively showed inhibition of decay development for more than 20 days (FIG. 8). These treatments resulted in less than 5% decay while that of the control was found to be greater than 95%. Additionally, less than 10% fruit decay occurred after treatment with a combination of 0.25% citral and 0.25% 1-octanol, or 0.25% citral and 0.25% sun treated crude, or 0.125% citral, 0.125% sun treated crude and 0.125% 1-octanol.

Example 12

Pure limonene was exposed to sunlight for three hours. A microbiocidal composition was prepared by dissolving the treated limonene in an aqueous solution containing 25% ethanol and a detergent (Tween 20). Lemons inoculated with *Penicillium* $10^4$ spores/ml were dipped for one minute once or up to four times one day after inoculation in the composition comprising the sunlight exposed limonene solution and stored at 20° C. Effect of the sun treated limonene on pathogen development on the fruit was checked daily during storage. FIG. 9 shows the effect of number of dips and length of each dip on decay reduction. Data suggest that the results are greatly affected by the amount of the material absorbed by the pathogen or the fruit tissues. This figure shows that limonene treated by sunlight gives better decay control after more or longer dips as compared to one dip.

Example 13

Pure limonene was irradiated with UV light (254 nm) for three hours. A microbiocidal composition was prepared by dissolving the treated limonene in an aqueous solution containing 25% ethanol and a detergent (Tween 20). Lemons inoculated with *Penicillium* $10^4$ spores/ml were dipped once or three times in the solution one day after inoculation for one minute in the irradiated solution and stored at 20° C. In the case of multi-dip, fruit were left to dry for one hour between two consecutive dips.

The effect of the ultra violet irradiation treated limonene on pathogen development on the fruit was checked during one month. FIG. 10 shows the similar decay inhibition by the 25% alcohol solution and the treatment of one dip in 2500 ppm of UV treated limonene (defined as 3UVL). The three consecutive dips in the UV treated limonene, (defined as 3UVL3) had much better decay control of all these treatments. The control solution is an aqueous solution containing Tween 20.

Example 14

Figure 14:
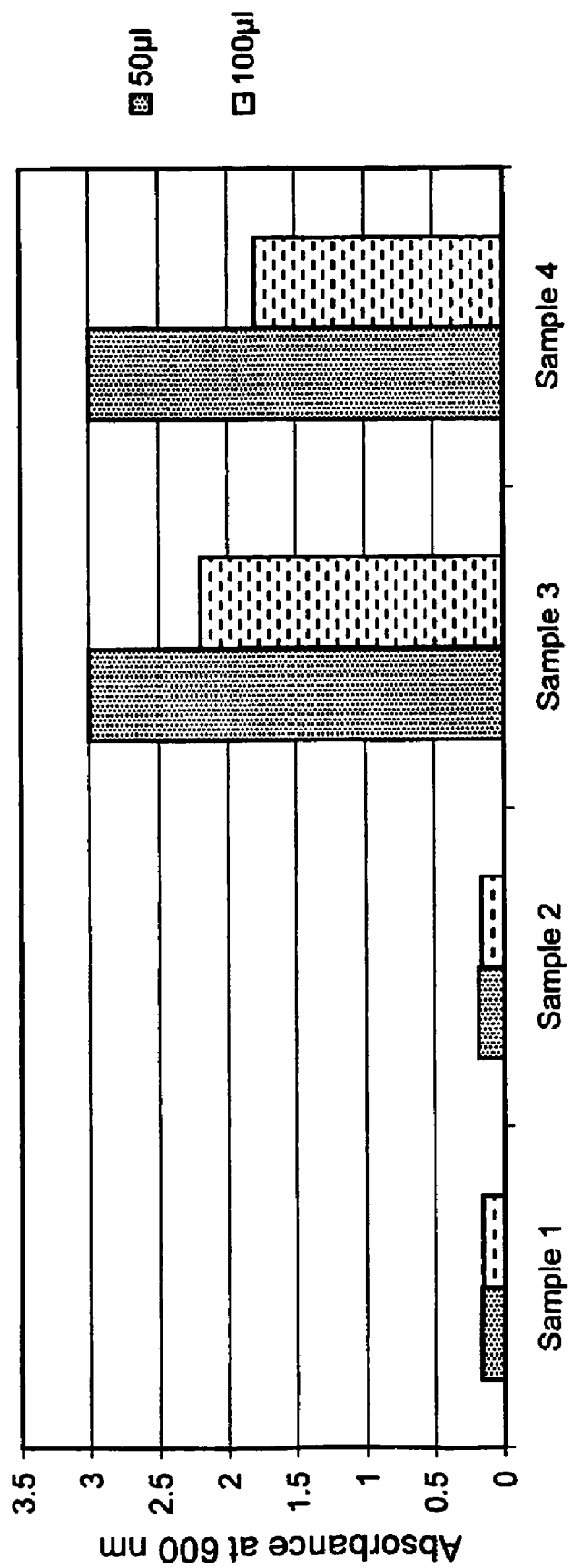
FIG. 14 Shows the effect of citral formulation on growth of *Staphylococcus aureus* cells.

Cells of wild type *Staphylococcus aureus* ($5 \times 10^8$, $OD_{600} = 0.219$) were grown for 3 hr in culture broth (cy/gp) at 37° C. with different concentration of extracts 50-100 μl. OD was determined at 600 nm. Sample 1 comprises of 2000 ppm citral, 25% ethanol and 2000 ppm Tween 20. Sample 2 comprises of the same substances as sample 1 together with β-CD 500 ppm and 300 ppm BHA. Both samples 1 and 2 significantly inhibited cell growth of *Staphylococus aureus*. The same compositions of substances without citral (SAMPLES 3,4) did not inhibit the growth of the pathogen (FIG. 14).

Example 15

Cells of wild type *Candida albicans* ($1 \times 10^3$) were grown on culture broth at 37° C. with different concentration of extracts 50-100 μl. OD was determined at 600 nm.

The following treatments in 6 different tubes were given:
TUBE 1. 2000 ppm Citral+25% Ethanol+2000 ppm Tween-20.
TUBE 2. 2000 ppm Citral+25% Ethanol+2000 ppm Tween-20+300 ppm BHA.
TUBE 3. 2000 ppm Sun-treated limonene+2000 ppm Tween-20.
TUBE 4. 2000 ppm Sun-treated limonene+25% ethanol+2000 ppm Tween-20.
TUBE 5. 25% ethanol+2000 ppm Tween-20.
TUBE 6. 25% ethanol+2000 ppm Tween-20+500 ppm β-CD+300 ppm BHA.

Figure 15:
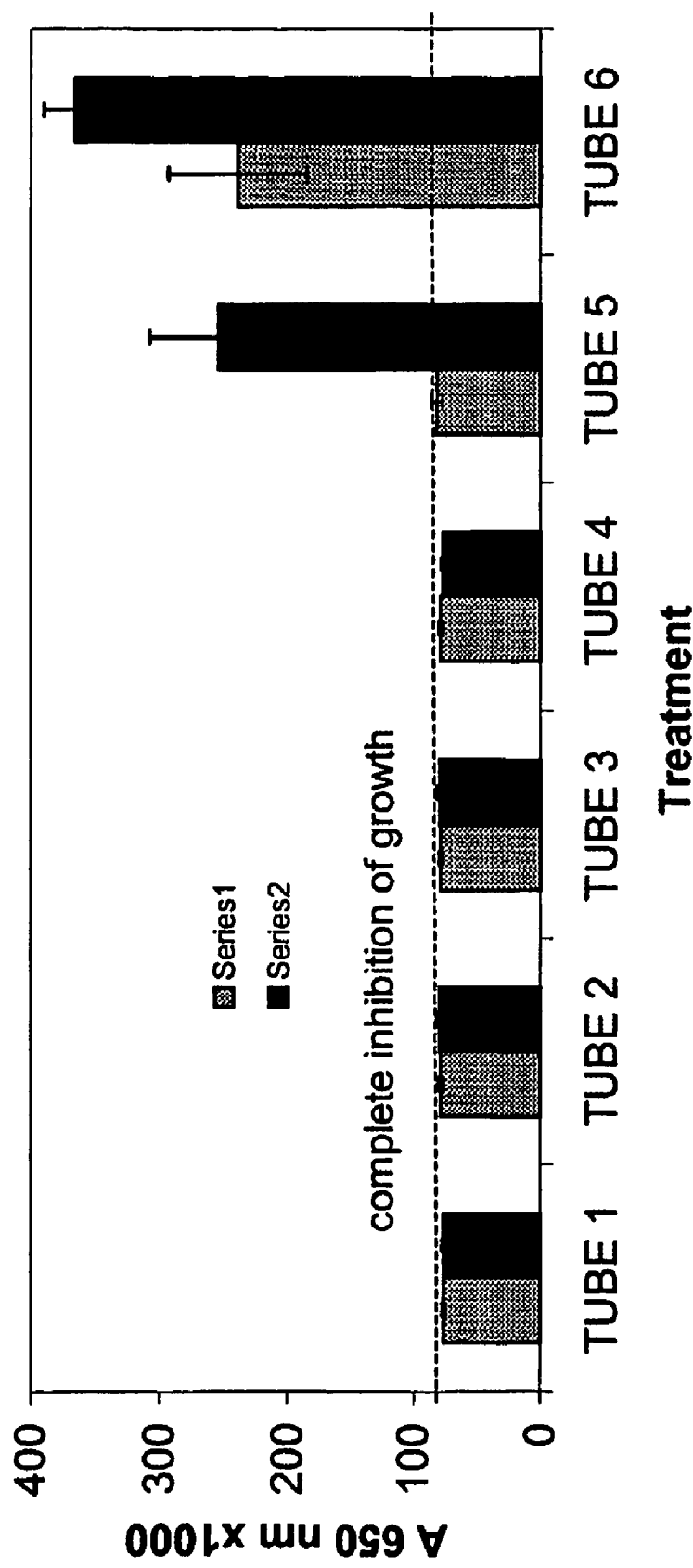
FIG. 15 Shows the effect of citral and sun-treated limonene on the growth of *Candida albicans* cells.

2000 ppm Citral in 25% ethanol and 2000 ppm Tween 20, or the same substances together with β-CD 500 ppm, 300 ppm BHA, or sun treated limonene dissolved in either 25% ethanol or 2000 ppm Tween 20 completely inhibited cell growth of this organism. The same compositions of substances without citral or sun treated limonene (Tubes 5 and 6) did not inhibit the growth of the pathogen (FIG. 15).

Although the invention has been described in conjunction with specific embodiments, it is evident that many alternatives and variations will be apparent to those skilled in the art in light of the foregoing description. Accordingly, the invention is intended to embrace all of the alternatives and variations that fall within the spirit and scope of the appended claims.

The invention claimed is:

1. A microbiocidal aqueous formulation, comprising:
   an aqueous formulation consisting of:
   (i) at least one essential oil component or derivative thereof present in a microbiocidal effective amount, the derivative thereof being obtained by exposure to light or by oxidation or a mixture thereof;
   (ii) at least one stabilizer selected from the group consisting of:
      (a) an antioxidant, selected from the group consisting of butylated hydroxyanisole (BHA), ascorbic acid, butylated hydroxytoluene (BHT) isoascorbic acid, $\alpha$-tocopherol, $\beta$-carotene, or mixtures thereof; and
      (b) an encapsulating agent selected from the group consisting of cornstarch, maltodextrin, silica gel, $\beta$-cyclodextrin, casein, chitosan and mixtures thereof;
   (iii) an aqueous solvent; and
   (iv) optionally an additional biocide,
   wherein the microbiocidal aqueous formulation does not comprise ethanol; and wherein when the at least one essential oil component or derivative thereof comprises citral, the citral is present at a concentration of from about 0.1% to about 1% v/v.

2. The microbiocidal aqueous formulation according to claim 1, wherein the essential oil component or derivative thereof is selected from the group consisting of a monoterpene hydrocarbon, a sesquiterpene hydrocarbon, an oxygenated terpene derivative, and a non-terpene derivative.

3. The microbiocidal aqueous formulation according to claim 1, wherein the non-terpene derivative comprises one or more members selected from the group consisting of an aldehyde, an alcohol, an acid, an ester, and a phenolic.

4. The microbiocidal aqueous formulation according to claim 2, wherein the essential oil component or derivative thereof is selected from the group consisting of citral, 1-octanol, heptanol, nonanol, geraniol, octanal, nonanal, decanal, perillaldehyde, perillalcohol, citronellol, citronellal, carvone, carveol, linalool, vanillin, cinnamic aldehyde, cinnamic acid, eugenol, menthol, limonene, limonene hydroperoxide, carvacrol, terpineol, thymol, and camphor.

5. The microbiocidal aqueous formulation according to claim 4, wherein the essential oil component or derivative thereof is selected from the group consisting of citral, geraniol, limonene, and limonene hydroperoxide.

6. The microbiocidal aqueous formulation according to claim 5, wherein the at least one essential oil component is present at a concentration of from about 0.1% to about 1.0% v/v.

7. The microbiocidal aqueous formulation according to claim 1, comprising the additional biocide at a concentration of from about 5 ppm to about 100 ppm.

8. The microbiocidal aqueous formulation according to claim 7, wherein the additional biocide is selected from the group consisting of imazalil, thiabendazole, panoctine, rovral, prochloraz, sodium orthophenylphenate, metalaxyl, phosetyl-al, captan, oxyquinoline, dicloran benzalkonium chloride, canon, thiophanate-methyl, triforine, carbendazim, triademinol, vinclozolin, etaconazole, and a mixture of any two or more thereof.

9. The microbiocidal aqueous formulation according to claim 8, wherein the essential oil component is citral, the stabilizer is an antioxidant, and the additional biocide is imazalil.

10. A method for inhibiting microbial development on a surface comprising the application to a surface of an effective amount of an aqueous formulation consisting of:
   i) at least one essential oil component or derivative thereof present in a microbiocidal effective amount, the derivative thereof being obtained by exposure to light or by oxidation or a mixture thereof;
   (ii) at least one stabilizer selected from the group consisting of:
      (a) an antioxidant, selected from the group consisting of butylated hydroxyanisole (BHA), ascorbic acid, butylated hydroxytoluene (BHT) isoascorbic acid, $\alpha$-tocopherol, $\beta$-carotene, or mixtures thereof; and
      (b) an encapsulating agent selected from the group consisting of cornstarch, maltodextrin, silica gel, $\beta$-cyclodextrin, casein, chitosan and mixtures thereof;
   (iii) an agueous solvent; and
   (iv) optionally an additional biocide,
   wherein the microbiocidal aqueous formulation does not comprise ethanol; and wherein when the at least one essential oil component or derivative thereof comprises citral, the citral is present at a concentration of from about 0.1% to about 1% v/v.

11. The method according to claim 10, for protecting fruits and vegetables from post harvest decay.

12. The microbiocidal aqueous formulation according to claim 5, wherein the at least one essential oil component is selected from the group consisting of citral and geraniol and is present at a concentration of from about 0.2% to about 0.4% v/v.

13. The microbiocidal aqueous formulation according to claim 10, wherein the at least one stabilizer is an antioxidant or an encapsulating agent.

* * * * *